(12) United States Patent
Morita et al.

(10) Patent No.: US 10,280,319 B2
(45) Date of Patent: *May 7, 2019

(54) INK, INK CARTRIDGE, INK JET RECORDING DEVICE, INK JET INK PRINTED MATTER, COMPOUND, AND COMPOSITION

(71) Applicant: RICOH COMPANY, LTD., Tokyo (JP)

(72) Inventors: Mitsunobu Morita, Kanagawa (JP); Soh Noguchi, Kanagawa (JP); Okitoshi Kimura, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/420,821

(22) Filed: Jan. 31, 2017

(65) Prior Publication Data

US 2017/0137644 A1   May 18, 2017

Related U.S. Application Data

(63) Continuation of application No. 14/287,789, filed on May 27, 2014, now Pat. No. 9,593,248.

(30) Foreign Application Priority Data

Jun. 5, 2013  (JP) .................. 2013-118869
Mar. 20, 2014  (JP) .................. 2014-057602

(51) Int. Cl.
  *C07C 233/20*  (2006.01)
  *C07C 233/49*  (2006.01)
  (Continued)

(52) U.S. Cl.
  CPC .......... *C09D 11/101* (2013.01); *C07C 233/20* (2013.01); *C07C 233/49* (2013.01); *C07D 211/22* (2013.01); *C07D 211/46* (2013.01); *C07D 295/195* (2013.01); *C07D 295/215* (2013.01); *C08F 22/38* (2013.01); *C08F 26/06* (2013.01); *C08F 120/56* (2013.01); *C08F 120/58* (2013.01); *C08F 120/60* (2013.01);
  (Continued)

(58) Field of Classification Search
  CPC ..... C09D 11/101; C09D 11/38; C09D 11/107; C09D 11/324; C09D 11/30; C08F 220/58; C08F 120/56; C08F 120/60; C08F 120/58; C08F 220/60; C08F 22/38; C08F 26/06; C08F 220/56; C08F 2220/585; C08F 2220/606; C07D 211/22; C07D 211/46; C07D 295/195; C07D 295/215; C08K 3/04; Y10T 428/24802; C07C 233/20; C07C 233/49
  See application file for complete search history.

(56) References Cited

U.S. PATENT DOCUMENTS 3,285,686 A   11/1966  Gunderson et al.
4,159,383 A   6/1979   Culbertson
(Continued)

FOREIGN PATENT DOCUMENTS

DE    879018     6/1953
EP    0 283 824 A2  9/1988
(Continued)

OTHER PUBLICATIONS

Office Action dated Oct. 10, 2017 in Japanese Patent Application No. 2014-057602.
(Continued)

*Primary Examiner* — Patrick D Niland
(74) *Attorney, Agent, or Firm* — Oblon, McClelland, Maier & Neustadt, L.L.P.

(57) ABSTRACT

Ink contains at least one of a compound represented by the following chemical formula 1, a compound represented by chemical formula 2, a compound represented by chemical formula 3, or a compound represented by chemical formula 4.

Chemical formula 1

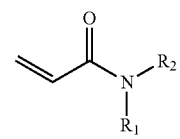

(1)

Chemical formula 2

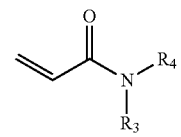

(2)

Chemical formula 3

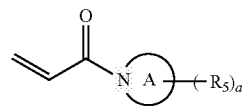

(3)

Chemical formula 4

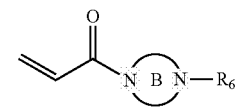

(4)

14 Claims, 1 Drawing Sheet

(51) Int. Cl.

| | | |
|---|---|---|
| C07D 211/22 | (2006.01) | |
| C07D 211/46 | (2006.01) | |
| C07D 295/195 | (2006.01) | |
| C07D 295/215 | (2006.01) | |
| C08F 22/38 | (2006.01) | |
| C08F 26/06 | (2006.01) | |
| C08F 120/56 | (2006.01) | |
| C08F 120/58 | (2006.01) | |
| C08F 120/60 | (2006.01) | |
| C08F 220/56 | (2006.01) | |
| C08F 220/58 | (2006.01) | |
| C08F 220/60 | (2006.01) | |
| C08K 3/04 | (2006.01) | |
| C09D 11/324 | (2014.01) | |
| C09D 11/30 | (2014.01) | |
| C09D 11/101 | (2014.01) | |
| C09D 11/107 | (2014.01) | |
| C09D 11/38 | (2014.01) | |

(52) U.S. Cl.
CPC .......... *C08F 220/58* (2013.01); *C08F 220/60* (2013.01); *C09D 11/107* (2013.01); *C09D 11/30* (2013.01); *C09D 11/324* (2013.01); *C09D 11/38* (2013.01); *C08F 220/56* (2013.01); *C08F 2220/585* (2013.01); *C08F 2220/606* (2013.01); *C08K 3/04* (2013.01); *Y10T 428/24802* (2015.01)

(56) References Cited

U.S. PATENT DOCUMENTS

| | | | |
|---|---|---|---|
| 4,866,151 | A | 9/1989 | Tsai et al. |
| 4,978,754 | A | 12/1990 | Ib et al. |
| 5,470,916 | A | 11/1995 | Righetti et al. |
| 5,716,739 | A | 2/1998 | Kashiwazaki et al. |
| 5,719,202 | A | 2/1998 | Share |
| 5,888,698 | A | 3/1999 | Koh |
| 6,180,560 | B1 | 1/2001 | Hayakawa et al. |
| 9,267,043 | B2 * | 2/2016 | Morita ............... C07C 233/09 |
| 9,593,248 | B2 * | 3/2017 | Morita ............... C08F 26/06 |
| 2004/0071187 | A1 | 4/2004 | Hayakawa et al. |
| 2004/0077754 | A1 | 4/2004 | Moszner et al. |
| 2009/0142710 | A1 * | 6/2009 | Lin ................... G03F 7/2018 430/322 |
| 2010/0313782 | A1 | 12/2010 | Loccufier et al. |
| 2011/0060100 | A1 | 3/2011 | Kimura et al. |
| 2011/0092610 | A1 | 4/2011 | Habashi et al. |
| 2012/0086762 | A1 | 4/2012 | Noguchi et al. |
| 2012/0147103 | A1 | 6/2012 | Hasegawa et al. |
| 2012/0176456 | A1 | 7/2012 | Maekawa et al. |
| 2012/0242768 | A1 | 9/2012 | Seno et al. |
| 2012/0283378 | A1 | 11/2012 | Shoshi et al. |
| 2013/0005849 | A1 | 1/2013 | Noguchi et al. |
| 2013/0065024 | A1 | 3/2013 | Aruga et al. |
| 2013/0144057 | A1 | 6/2013 | Morita |
| 2013/0267625 | A1 | 10/2013 | Noguchi et al. |
| 2014/0045965 | A1 | 2/2014 | Noguchi et al. |
| 2014/0050858 | A1 | 2/2014 | Loccufier et al. |
| 2014/0120326 | A1 | 5/2014 | Morita et al. |

FOREIGN PATENT DOCUMENTS

| | | |
|---|---|---|
| EP | 1 374 829 A1 | 1/2004 |
| EP | 2 053 101 A1 | 4/2009 |
| EP | 2 267 048 A1 | 12/2010 |
| EP | 2 604 636 A1 | 6/2013 |
| EP | 2 725 009 A1 | 4/2014 |
| JP | 48-85222 A | 11/1973 |
| JP | 1-249750 A | 10/1989 |
| JP | 1-250371 A | 10/1989 |
| JP | 2-304071 A | 12/1990 |
| JP | 3-200815 | 9/1991 |
| JP | 4-211461 | 8/1992 |
| JP | 7-48524 | 2/1995 |
| JP | 7-501563 A | 2/1995 |
| JP | 8-227011 A | 9/1996 |
| JP | 10-115923 A | 5/1998 |
| JP | 10-310724 | 11/1998 |
| JP | 2001-206912 A | 7/2001 |
| JP | 2001-270973 | 10/2001 |
| JP | 2002-212244 | 7/2002 |
| JP | 2002-332431 | 11/2002 |
| JP | 2003-013046 | 1/2003 |
| JP | 2003-140341 | 5/2003 |
| JP | 2004-107653 | 4/2004 |
| JP | 2004-323753 A | 11/2004 |
| JP | 2005-514338 | 5/2005 |
| JP | 2005-247964 | 9/2005 |
| JP | 2006-504819 | 2/2006 |
| JP | 2006-111860 | 4/2006 |
| JP | 2007-332333 | 12/2007 |
| JP | 2008-509967 | 4/2008 |
| JP | 2008-105393 | 5/2008 |
| JP | 2008-156443 | 7/2008 |
| JP | 2009-067926 | 4/2009 |
| JP | 2009-144057 | 7/2009 |
| JP | 2010-013506 | 1/2010 |
| JP | 2010-058405 | 3/2010 |
| JP | 2010-069623 | 4/2010 |
| JP | 2010-138332 | 6/2010 |
| JP | 2010-229188 | 10/2010 |
| JP | 2012-025862 | 2/2012 |
| JP | 2012-117015 | 6/2012 |
| JP | 2012-140550 | 7/2012 |
| JP | 2012-144712 | 8/2012 |
| JP | 2013-53082 A | 3/2013 |
| WO | WO 00/07002 A1 | 2/2000 |
| WO | WO2003/035013 A1 | 5/2003 |
| WO | WO2004/039901 A1 | 5/2004 |
| WO | WO2006/018405 A1 | 2/2006 |
| WO | WO 2010/002450 A2 | 1/2010 |
| WO | WO 2013/122329 A1 | 8/2013 |

OTHER PUBLICATIONS

U.S. Appl. No. 09/689,523, filed Oct. 12, 2000.
Partial European Search Report dated Oct. 31, 2014 in Patent Application No. 14170493.2.
Vadim V. Annenkov et al., "Synthesis of Biomimetic Polyamines", ARKIVOK, vol. 2009, No. 13, XP-055147175, Jan. 1, 2009, pp. 116-130.
Database Registry [Online] Chemical Abstracts Service, Columbus, Ohio, US; "2-Propenamide, N -[2-( diethylamino)-2-oxoethyl]-N-methyl-", Oct. 13, 2009, 1 page.
Extended Search Report dated May 18, 2015 in European Patent Application No. 14170493.2.
Epton et al., "Poly[N-acryloyl-N,N-bis(2,2-dimethoxyethyl)amine]-{poly[bis(2,2-dimethoxyethyl)caramoylethylene]}", Macromolecular Syntheses, John Wiley & Sons Inc. New York, US, vol. 8, Jan. 1, 1982, pp. 95-98.
Boyd, et al., "Preparation of acrylamide amino acid derivatives as VLA-1 integrin antagonists", Database Caplus [Online] Chemical Abstracts Service, Columbus, Ohio, US; Feb. 24, 2005, XP002738887, Database accession No. 2005 : 158638 * abstract * * Registry-No. RN 845907-79-1,formula last page *.
Combined Office Action and Search Report dated Aug. 17, 2015 in Chinese Patent Application No. 201410241857.2 with English translation of category of cited documents.
Machine English translation of JP 2011-323753, Awaji et al., Nov. 2004.

* cited by examiner

INK, INK CARTRIDGE, INK JET RECORDING DEVICE, INK JET INK PRINTED MATTER, COMPOUND, AND COMPOSITION

CROSS-REFERENCE TO RELATED APPLICATIONS

This patent application is based on and claims priority pursuant to 35 U.S.C. § 119 to Japanese Patent Application Nos. 2013-118869 and 2014-057602, on Jun. 5, 2013 and Mar. 20, 2014, respectively, in the Japan Patent Office, the entire disclosures of which are hereby incorporated by reference herein.

BACKGROUND

Technical Field

The present invention relates to ink, an ink cartridge, an ink jet recording device, an ink jet ink printed matter, a compound, and a composition.

Background Art

An ink jet recording system is known as a method of forming an image on a recording medium, typically paper. The ink jet recording system has an excellent consumption efficiency and excellent resource saving properties, resulting in low cost of ink per recording unit.

In recent years, ink jet recording system using ultraviolet curing ink has become appealing.

JP-2009-67926-A discloses an ink composition for ink jet recording and the ink composition contains: (A) aliphatic (meth)acrylate compound having a secondary hydroxyl group; (B): a compound having a nitrogen atom and a polymerizable unsaturated bond in its molecule; and (C): a radical polymerization initiator.

JP2009-144057-A discloses an ink composition for ink jet recording containing: (A): a polymerizable compound and (B): a radical polymerization initiator. As the polymerizable compound (A) contains a polymerizable compound (A1) having a polymerizable unsaturated bond and an amino group in its molecule. In addition, the ratio of a monofunctional polymerizable monomer to the total amount of the polymerizable compound (A) ranges from 90% by weight to 99.9% by weight and the ratio of a multi-functional monomer to the total amount of the polymerizable compound (A) ranges from 0.1% by weight to 10% by weight.

Although these are successful to some degree, a compound having excellent polymerization property and photo-curability with less odor and small viscosity is demanded.

SUMMARY

The present invention provides an improved Ink that contains at least one of a compound represented by chemical formula 1, a compound represented by chemical formula 2, a compound represented by chemical formula 3, and a compound represented by chemical formula 4

Chemical formula 1

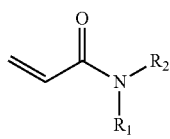

(1)

where $R_1$ represents a hydrocarbon group having 1 to 10 carbon atoms and $R_2$ represents a monovalent group containing a group represented by —$OX_1$, where $X_1$ represents a monovalent hydrocarbon group having 1 to 10 carbon atoms, a monovalent group containing a group represented by —$COOX_2$, where $X_2$ represents a monovalent hydrocarbon group having 1 to 10 carbon atoms, a monovalent group containing a group represented by —$OCOX_3$, where $X_3$ represents a monovalent hydrocarbon group having 1 to 10 carbon atoms, a monovalent group containing a group represented by —$NX_4X_5$, where $X_4$ and $X_5$ each, independently represent monovalent hydrocarbon groups having 1 to 10 carbon atoms, a monovalent group containing a group represented by —$CONX_6X_7$, where $X_6$ and $X_7$ each, independently represent monovalent hydrocarbon groups having 1 to 10 carbon atoms, or a monovalent group containing a hydroxyl group, Chemical formula 2

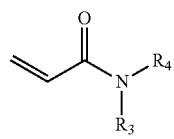

(2)

where, $R_3$ and $R_4$ each, independently represent monovalent groups containing groups represented by —$OX_1$, where $X_1$ represents a monovalent hydrocarbon group having 1 to 10 carbon atoms, a monovalent group containing a group represented by —$COOX_2$, where $X_2$ represents a monovalent hydrocarbon group having 1 to 10 carbon atoms, a monovalent group containing a group represented by —$OCOX_3$, where $X_3$ represents a monovalent hydrocarbon group having 1 to 10 carbon atoms, a monovalent group containing a group represented by —$NX_4X_5$, where $X_4$ and $X_5$ each, independently represent monovalent hydrocarbon groups having 1 to 10 carbon atoms, a monovalent group containing a group represented by —$CONX_6X_7$, where $X_6$ and $X_7$ each, independently represent monovalent hydrocarbon groups having 1 to 10 carbon atoms, or a monovalent group containing a hydroxyl group, Chemical formula 3

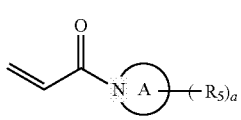

(3)

where the ring A represents a saturated five-membered ring or a saturated six-membered ring, both containing a nitrogen atom, $R_5$ represents a monovalent group containing a group represented by —$OX_1$, where $X_1$ represents a monovalent hydrocarbon group having 1 to 10 carbon atoms, a monovalent group containing a group represented by —$COOX_2$, where $X_2$ represents a monovalent hydrocarbon group having 1 to 10 carbon atoms, a monovalent group containing a group represented by —$OCOX_3$, where $X_3$ represents a monovalent hydrocarbon group having 1 to 10 carbon atoms, a monovalent group containing a group represented by —$NX_4X_5$, where $X_4$ and $X_5$ each, independently represent monovalent hydrocarbon groups having 1 to 10 carbon atoms, a monovalent group containing a group represented by —CONX$_6$X$_7$, where X$_6$ and X$_7$ each, independently represent monovalent hydrocarbon groups having 1 to 10 carbon atoms, or a monovalent group containing a hydroxyl group, and a is 1, 2, or 3, and Chemical formula 4

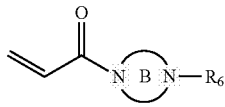

(4)

where the ring B represents a saturated five-membered ring or a saturated six-membered ring, both containing two nitrogen atoms, R$_6$ represents a monovalent group containing a group represented by —OX$_1$, where X$_1$ represents a monovalent hydrocarbon group having 1 to 10 carbon atoms, a monovalent group containing a group represented by —COOX$_2$, where X$_2$ represents a monovalent hydrocarbon group having 1 to 10 carbon atoms, a monovalent group containing a group represented by —OCOX$_3$, where X$_3$ represents a monovalent hydrocarbon group having 1 to 10 carbon atoms, a monovalent group containing a group represented by —NX$_4$X$_5$, where X$_4$ and X$_5$ each, independently represent monovalent hydrocarbon groups having 1 to 10 carbon atoms, a monovalent group containing a group represented by —CONX$_6$X$_7$, where X$_6$ and X$_7$ each, independently represent monovalent hydrocarbon groups having 1 to 10 carbon atoms, a monovalent group containing a hydroxyl group, or an alkyl group having 1 to 10 carbon atoms.

BRIEF DESCRIPTION OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein.

DETAILED DESCRIPTION

Figure 1:
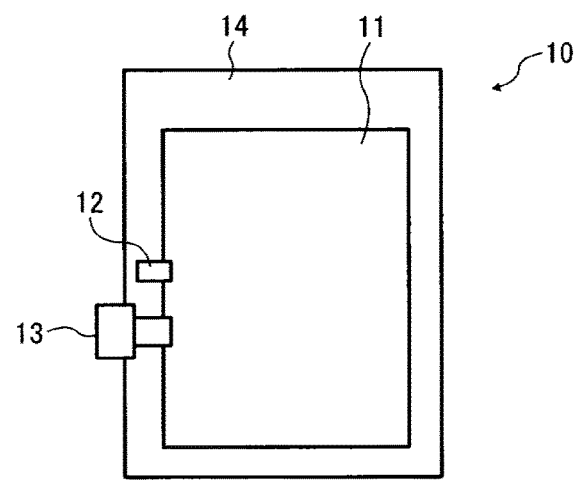
FIG. 1 is a diagram illustrating an example of the ink cartridge according to an embodiment of the present invention.

The present invention is to provide a compound and ink and a composition that contain the ink, which have excellent polymerization property and photocurability with less odor and low viscosity Next, embodiments of the present disclosure are described with reference to accompanying drawings.

The ink of the present disclosure contains at least one of a compound represented by chemical formula 1, a compound represented by chemical formula 2, a compound represented by chemical formula 3, and a compound represented by chemical formula 4.

Chemical formula 1

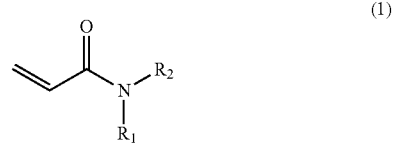

(1)

In chemical formula 1, R$_1$ represents a hydrocarbon group having 1 to 10 carbon atoms and R$_2$ represents a monovalent group containing a group represented by —OX$_1$, where X$_1$ represents a monovalent hydrocarbon group having 1 to 10 carbon atoms, a monovalent group having a group represented by —COOX$_2$, where X$_2$ represents a monovalent hydrocarbon group having 1 to 10 carbon atoms, a monovalent group having a group represented by —OCOX$_3$, where X$_3$ represents a monovalent hydrocarbon group having 1 to 10 carbon atoms, a monovalent group having a group represented by —NX$_4$X$_5$, where X$_4$ and X$_5$ each, independently represent monovalent hydrocarbon groups having 1 to 10 carbon atoms, a monovalent group containing a group represented by —CONX$_6$X$_7$, where X$_6$ and X$_7$ each, independently represent monovalent hydrocarbon groups having 1 to 10 carbon atoms, or a monovalent group containing a hydroxyl group.

Chemical formula 2

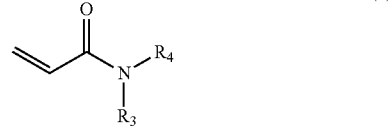

(2)

In chemical formula 2, R$_3$ and R$_4$ each, independently represent monovalent groups containing groups represented by —OX$_1$, where X$_1$ represents a monovalent hydrocarbon group having 1 to 10 carbon atoms, a monovalent group having a group represented by —COOX$_2$, where X$_2$ represents a monovalent hydrocarbon group having 1 to 10 carbon atoms, a monovalent group having a group represented by —OCOX$_3$, where X$_3$ represents a monovalent hydrocarbon group having 1 to 10 carbon atoms, a monovalent group having a group represented by —NX$_4$X$_5$, where X$_4$ and X$_5$ each, independently represent monovalent hydrocarbon groups having 1 to 10 carbon atoms, a monovalent group containing a group represented by —CONX$_6$X$_7$, where X$_6$ and X$_7$ each, independently represent monovalent hydrocarbon groups having 1 to 10 carbon atoms, or a monovalent group containing a hydroxyl group.

Chemical formula 3

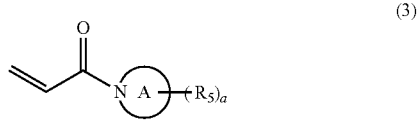

(3)

In chemical formula 3, the ring A represents a saturated five-membered ring or a saturated six-membered ring, both containing a nitrogen atom, R$_5$ represents a monovalent group containing a group represented by —OX$_1$, where X$_1$ represents a monovalent hydrocarbon group having 1 to 10 carbon atoms, a monovalent group having a group represented by —COOX$_2$, where X$_2$ represents a monovalent hydrocarbon group having 1 to 10 carbon atoms, a monovalent group having a group represented by —OCOX$_3$, where X$_3$ represents a monovalent hydrocarbon group having 1 to 10 carbon atoms, a monovalent group having a group represented by —NX$_4$X$_5$, where X$_4$ and X$_5$ each, independently represent monovalent hydrocarbon groups having 1 to 10 carbon atoms, a monovalent group containing a group represented by —CONX$_6$X$_7$, where X$_6$ and X$_7$ each, independently represent monovalent hydrocarbon groups having 1 to 10 carbon atoms, or a monovalent group containing a hydroxyl group, and a is 1, 2, or 3.

Chemical formula 4

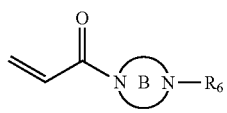

(4)

In chemical formula 4, the ring B represents a saturated five-membered ring or a saturated six-membered ring, both containing two nitrogen atoms, R$_6$ represents a monovalent group containing a group represented by —OX$_1$, where X$_1$ represents a monovalent hydrocarbon group having 1 to 10 carbon atoms, a monovalent group having a group represented by —COOX$_2$, where X$_2$ represents a monovalent hydrocarbon group having 1 to 10 carbon atoms, a monovalent group having a group represented by —OCOX$_3$, where X$_3$ represents a monovalent hydrocarbon group having 1 to 10 carbon atoms, a monovalent group containing a group represented by —NX$_4$X$_5$, where X$_4$ and X$_5$ each, independently represent monovalent hydrocarbon groups having 1 to 10 carbon atoms, a monovalent group containing a group represented by —CONX$_6$X$_7$, where X$_6$ and X$_7$ each, independently represent monovalent hydrocarbon groups having 1 to 10 carbon atoms, a monovalent group containing a hydroxyl group, or an alkyl group having 1 to 10 carbon atoms.

The compound represented by chemical formula 1, the compound represented by chemical formula 2, the compound represented by chemical formula 3, and the compound represented by chemical formula 4 have no carbonyl imino group (—CONH—) but a monovalent group having a group represented by —OX$_1$, where X$_1$ represents a monovalent hydrocarbon group having 1 to 10 carbon atoms, a monovalent group having a group represented by —COOX$_2$, where X$_2$ represents a monovalent hydrocarbon group having 1 to 10 carbon atoms, a monovalent group having a group represented by —OCOX$_3$, where X$_3$ represents a monovalent hydrocarbon group having 1 to 10 carbon atoms, a monovalent group having a group represented by —NX$_4$X$_5$, where X$_4$ and X$_5$ each, independently represent monovalent hydrocarbon groups having 1 to 10 carbon atoms, a monovalent group having a group represented by —CONX$_6$X$_7$, where X$_6$ and X$_7$ each, independently represent monovalent hydrocarbon groups having 1 to 10 carbon atoms, or a monovalent group containing a hydroxyl group. For this reason, these compounds have excellent polymerization property and photocurability with less odor and low viscosity. Accordingly, such compounds represented by chemical formula 1, 2, 3, or 4 are suitable for use in ink.

Since its intermolecular interaction is strong, an acrylamide having a carbonyl imino group has little odor but high viscosity, thereby becoming solid in some cases. For this reason, such an acrylamide is not suitable for use in ink.

An acrylamide which has no carbonyl imino group and a polar group not bonded with a nitrogen bond has high volatility and significant odor. For this reason, such an acrylamide is not suitable for use in ink.

An acrylamide having a ring structure in its molecule is preferable. In such an acrylamide, hardness is imparted to a photopolymerized material thereof, resulting in improvement of photocurability.

There is no specific limit to such a ring structure. Specific examples thereof include, but are not limited to, an aliphatic ring, a heterocyclic ring, and an aromatic ring. Of these, a heterocyclic ring is preferable, a ring containing a nitrogen atom is more preferable, and the ring A and the ring B are particularly preferable.

If a heterocyclic ring is introduced into the molecule of an acrylamide, the distance between molecules during polymerization becomes short due to polarization caused by the presence of the hetero atoms, which promotes photopolymerization. In addition, in terms of interaction between molecules, if a ring containing hetero atoms is introduced into the molecule of an acrylamide, hardness after photopolymerization is considered to become excellent.

An acrylamide having an oxy group or a carbonyl oxy group is preferable. An acrylamide having a carbonyl oxy group is more preferable. By having a such a structure, photocurability is further improved.

In the compound represented by chemical formula 1, there is no specific limit to R$_1$, X$_1$, X$_2$, X$_3$, X$_4$, X$_5$, X$_6$, and X$_7$. Specific examples thereof include, but are not limited to, a methyl group, an ethyl group, an n-propyl group, an isopropyl group, a t-butyl group, an n-pentyl group, an n-hexyl group, a cyclohexyl group, a phenyl group, and a benzyl group.

R$_1$ is preferably a cycloalkyl group, an aryl group, or an aralkyl group. If R$_1$ is such a group, photocurability is improved.

R$_2$ is preferably a 2-hydroxyethyl group (—CH$_2$CH$_2$OH) or a group represented by the following chemical formula 5.

Chemical formula 5

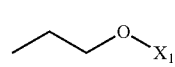

(5)

The viscosity of the compound represented by chemical formula 1 is further decreased by using such a group.

In the compound represented by chemical formula 2, X$_1$, X$_2$, X$_3$, X$_4$, X$_5$, X$_6$, and X$_7$ are the same as above.

R$_3$ and R$_4$ are preferably 2-hydroxyethyl groups or groups represented by chemical formula 5, independently. The viscosity of the compound represented by chemical formula 2 is further decreased by having such a group.

In the compound represented by chemical formula 3, X$_1$, X$_2$, X$_3$, X$_4$, X$_5$, X$_6$, and X$_7$ are the same as above.

A preferable compound represented by chemical formula 3 is represented by the following chemical formula 6.

Chemical formula 6

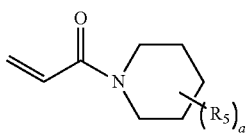

If such a compound is used as the compound represented by chemical formula 3, photocurability and photopolymerization properties are further improved.

$R_5$ is preferably a group represented by —$COOX_2$, where $X_2$ represents a hydrocarbon group having 1 to 10 carbon atoms and more preferably an ethyloxy carbonyl group (—$COOCH_2CH_3$). If $R_5$ is such a group, photocurability and photopolymerization properties are further improved.

In the compound represented by chemical formula 4, $X_1$, $X_2$, $X_3$, $X_4$, $X_5$, $X_6$, and $X_7$ are the same as above.

There is no specific limit to the hydrocarbon group having 1 to 10 carbon atoms as $R_5$. Specific examples thereof include, but are not limited to, a methyl group, an ethyl group, an n-propyl group, an isopropyl group, a t-butyl group, an n-pentyl group, an n-hexyl group, a cyclohexyl group, a phenyl group, and a benzyl group.

In the compound represented by chemical formula 1, there is no specific limit to the compound having a monovalent group containing a group represented by —$OX_1$ (where $X_1$ represents a monovalent hydrocarbon group having 1 to 10 carbon atoms) as $R_2$. Specific examples thereof include, but are not limited to, compounds represented by the following chemical formulae (where n is an integer of from 1 to 4, multiple $X_1$s are independent from each other).

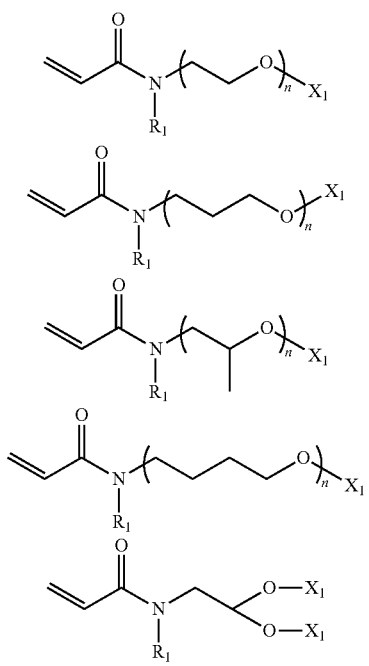

In the compound represented by chemical formula 2, there is no specific limit to the compound independently having monovalent groups containing groups represented by —$OX_1$ (where $X_1$ represents a monovalent hydrocarbon group having 1 to 10 carbon atoms) as $R_3$ and $R_4$. Specific examples thereof include, but are not limited to, compounds represented by the following chemical formulae (where n and m each, independently represent integers of from 1 to 4, multiple $X_1$s are independent from each other).

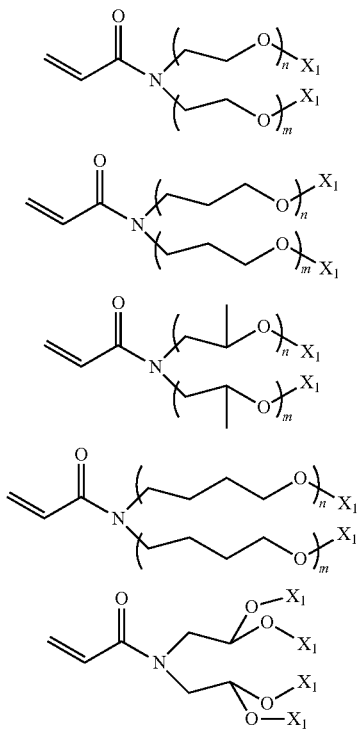

In the compound represented by chemical formula 1, there is no specific limit to the compound having a monovalent group containing a hydroxyl group as $R_2$. Specific examples thereof include, but are not limited to, compounds represented by the following chemical formulae (where n is an integer of from 1 to 4).

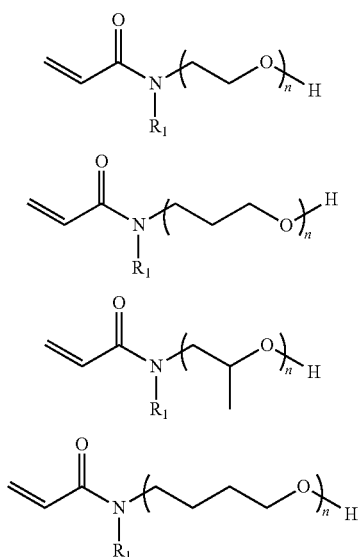

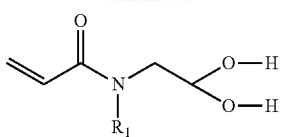

In the compound represented by chemical formula 2, there is no specific limit to the compound independently having monovalent groups containing hydroxyl groups as $R_3$ and $R_4$. Specific examples thereof include, but are not limited to, compounds represented by the following chemical formulae (where n and m each, independently represent integers of from 1 to 4).

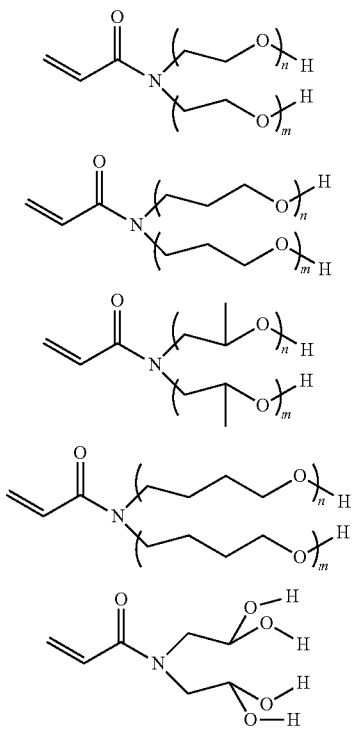

In the compound represented by chemical formula 1, there is no specific limit to the compound having a monovalent group containing a group represented by $-COOX_2$ (where $X_2$ represents a monovalent hydrocarbon group having 1 to 10 carbon atoms) as $R_2$. Specific examples thereof include, but are not limited to, compounds represented by the following chemical formulae.

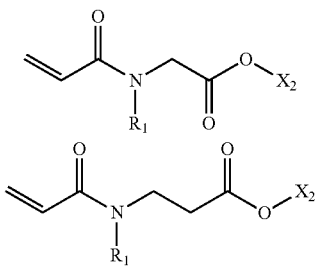

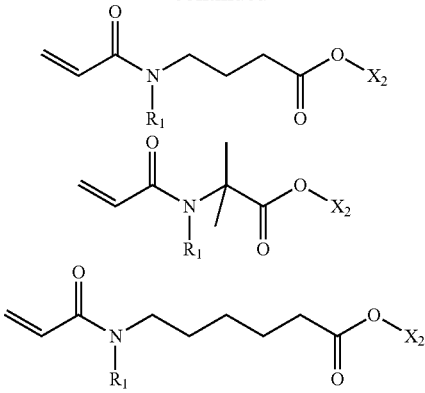

In the compound represented by chemical formula 2, there is no specific limit to the compound independently having monovalent groups containing groups represented by $-COOX_2$ (where $X_2$ represents a monovalent hydrocarbon group having 1 to 10 carbon atoms) as $R_3$ and $R_4$. Specific examples thereof include, but are not limited to, compounds represented by the following chemical formulae (where multiple $X_2$s are independent from each other).

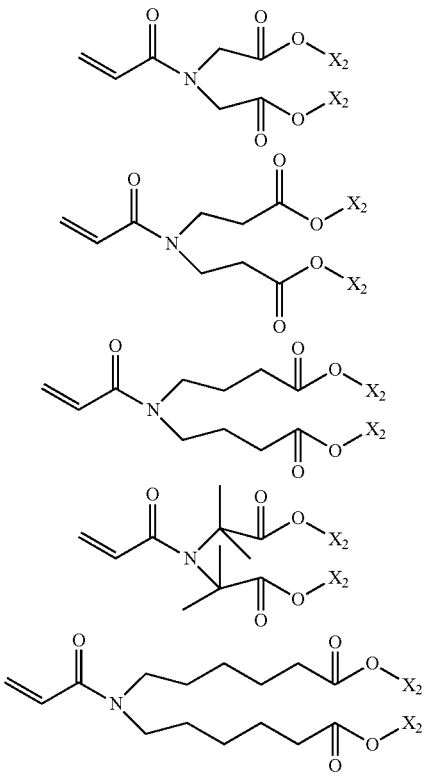

In the compound represented by chemical formula 1, there is no specific limit to the compound having a monovalent group containing a group represented by $-OCOX_3$ (where $X_3$ represents a monovalent hydrocarbon group having 1 to 10 carbon atoms) as $R_2$. Specific examples thereof include, but are not limited to, compounds represented by the following chemical formulae (where n is an integer of from 1 to 4, multiple $X_3$s are independent from each other).

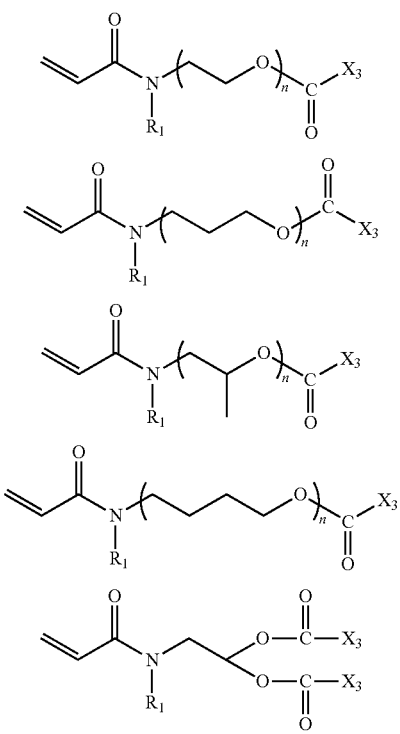

In the compound represented by chemical formula 2, there is no specific limit to the compound independently having monovalent groups containing groups represented by —$OCOX_3$ (where $X_3$ represents a monovalent hydrocarbon group having 1 to 10 carbon atoms) as $R_3$ and $R_4$. Specific examples thereof include, but are not limited to, compounds represented by the following chemical formulae (where n and m each, independently represent integers of from 1 to 4, multiple $X_3$s are independent from each other).

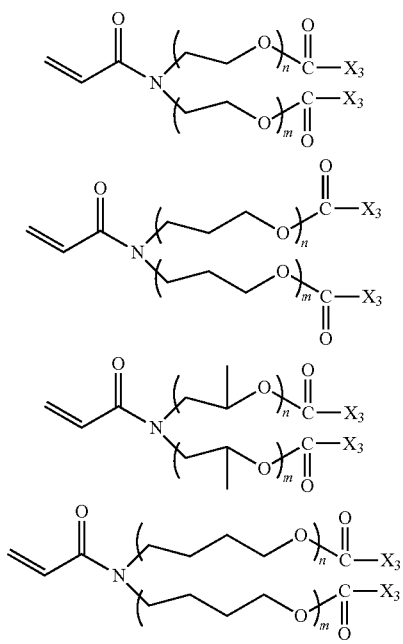

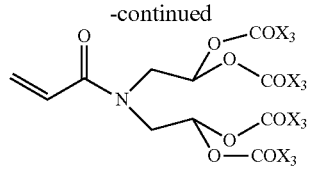

In the compound represented by chemical formula 1, there is no specific limit to the compound independently having monovalent groups containing groups represented by —$NX_4X_5$ (where $X_4$ and $X_5$ each, independently represent monovalent hydrocarbon groups having 1 to 10 carbon atoms) as $R_2$. Specific examples thereof include, but are not limited to, compounds represented by the following chemical formulae.

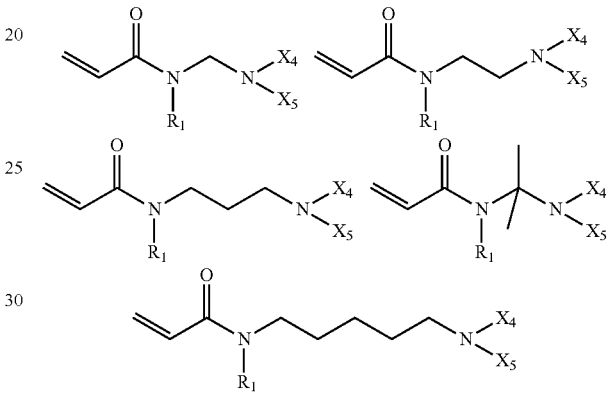

In the compound represented by chemical formula 2, there is no specific limit to the compound independently having monovalent groups containing groups represented by —$NX_4X_5$ (where $X_4$ and $X_5$ represent monovalent hydrocarbon groups having 1 to 10 carbon atoms) as $R_3$ and $R_4$. Specific examples thereof include, but are not limited to, compounds represented by the following chemical formulae (where multiple $X_4$s and $X_5$s each, are independent from each other).

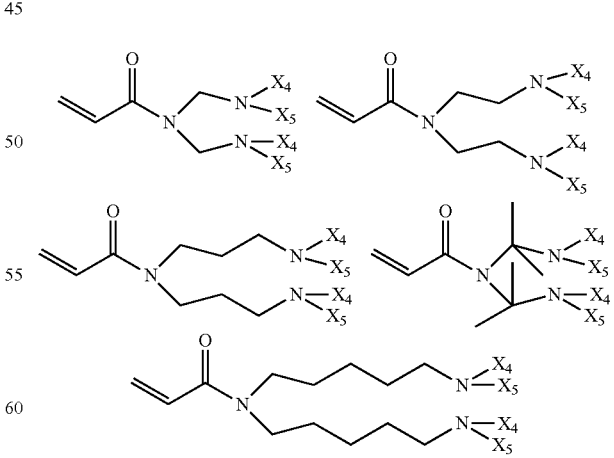

In the compound represented by chemical formula 1, there is no specific limit to the compound independently having monovalent groups containing groups represented by —$CONX_6X_7$ (where $X_6$ and $X_7$ each, independently represent monovalent hydrocarbon groups having 1 to 10 carbon atoms) as $R_2$. Specific examples thereof include, but are not limited to, compounds represented by the following chemical formulae.

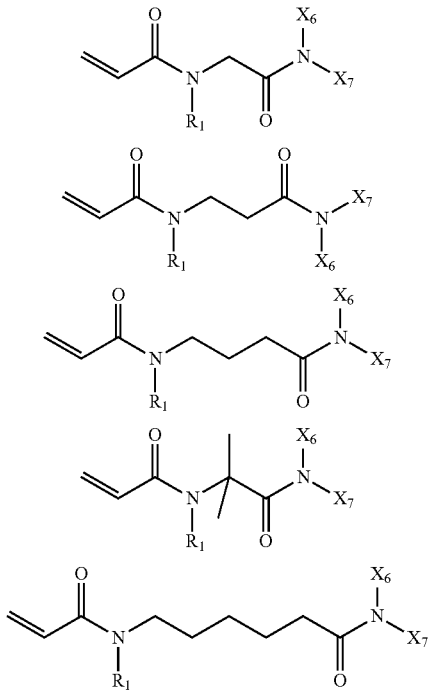

In the compound represented by chemical formula 2, there is no specific limit to the compound independently having monovalent groups containing groups represented by —$CONX_6X_7$ (where $X_6$ and $X_7$ each, independently represent monovalent hydrocarbon groups having 1 to 10 carbon atoms) as $R_3$ and $R_4$. Specific examples thereof include, but are not limited to, compounds represented by the following chemical formulae (where multiple $X_6$s and $X_7$s each, are independent from each other).

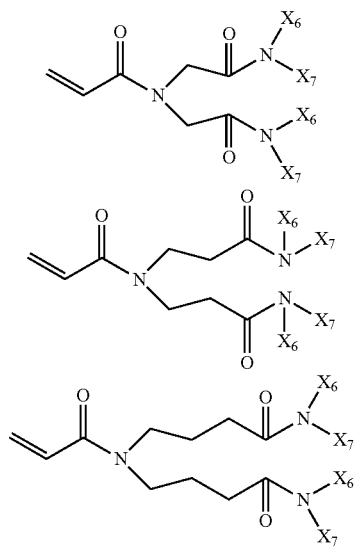

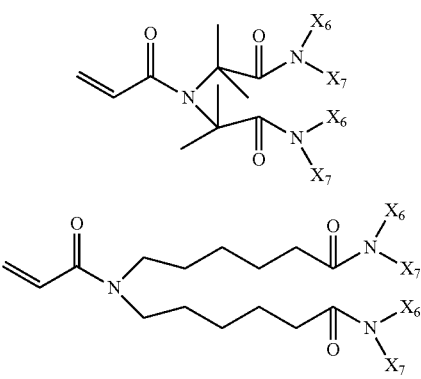

In the compound represented by chemical formula 3, there is no specific limit to the compound independently having monovalent groups containing groups represented by —$NX_4X_5$ (where $X_4$ and $X_5$ each, independently represent monovalent hydrocarbon groups having 1 to 10 carbon atoms) as $R_5$. Specific examples thereof include, but are not limited to, compounds represented by the following chemical formulae (where m represents 0 or an integer of from 1 to 6).

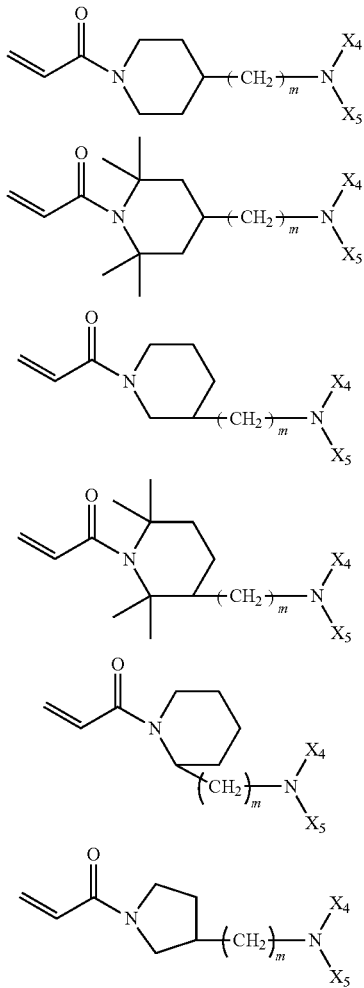

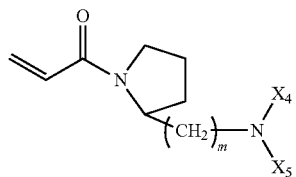

In the compound represented by chemical formula 3, there is no specific limit to the compound having a monovalent group containing a group represented by —$OX_1$ (where $X_1$ represents a monovalent hydrocarbon group having 1 to 10 carbon atoms) as $R_5$. Specific examples thereof include, but are not limited to, compounds represented by the following chemical formulae (where Y is a hydrogen atom or a methyl group, n is an integer of from 1 to 4, and m represents 0 or an integer of from 1 to 6).

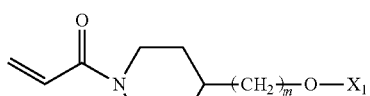
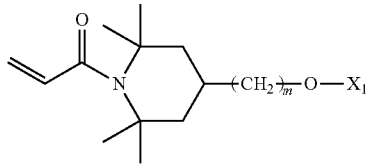
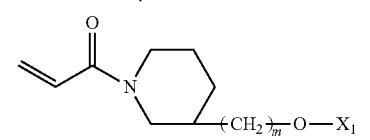
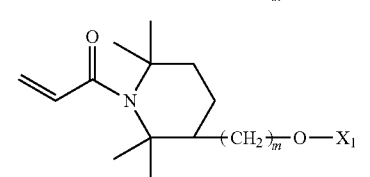
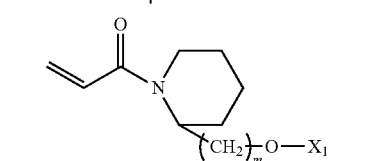
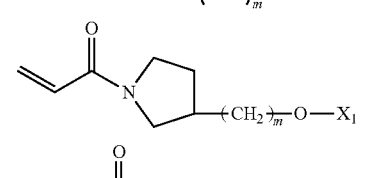
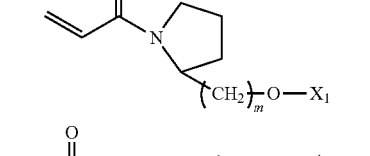
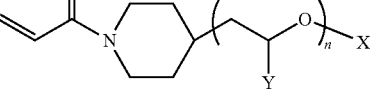
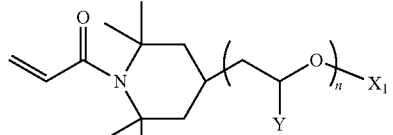
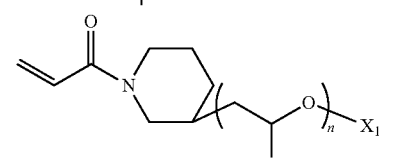
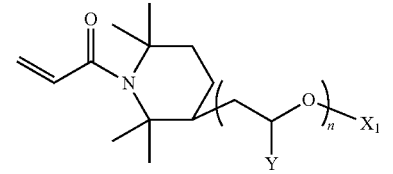
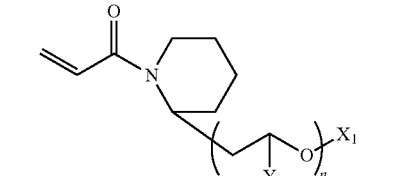
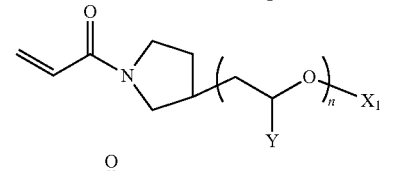
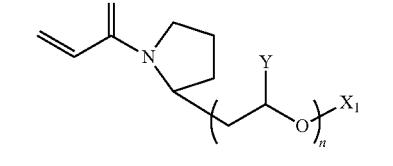

In the compound represented by chemical formula 3, there is no specific limit to the compound having a monovalent group containing a group represented by —$COOX_2$ (where $X_2$ represents a monovalent hydrocarbon group having 1 to 10 carbon atoms) as $R_5$. Specific examples thereof include, but are not limited to, compounds represented by the following chemical formulae (where m represents 0 or an integer of from 1 to 6).

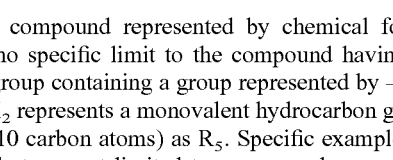
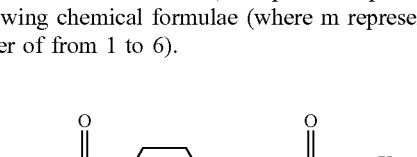
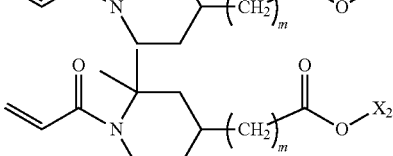
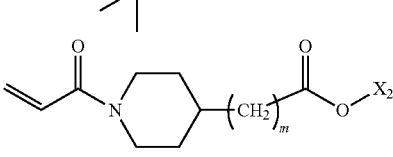

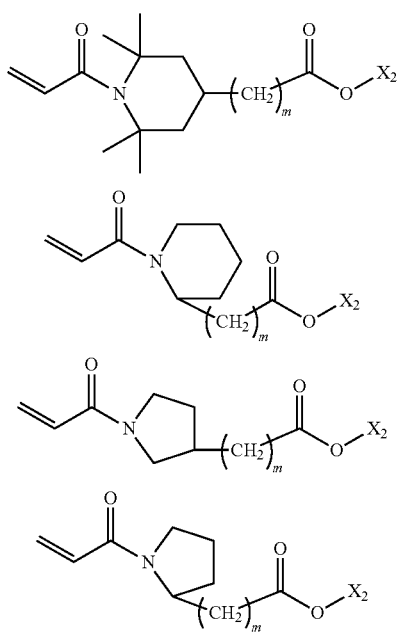

In the compound represented by chemical formula 3, there is no specific limit to the compound having a monovalent group containing a group represented by —OCOX$_3$ (where X$_3$ represents a monovalent hydrocarbon group having 1 to 10 carbon atoms) as R$_5$. Specific examples thereof include, but are not limited to, compounds represented by the following chemical formulae (where Y is a hydrogen atom or a methyl group, n is an integer of from 1 to 4, and m represents 0 or an integer of from 1 to 6).

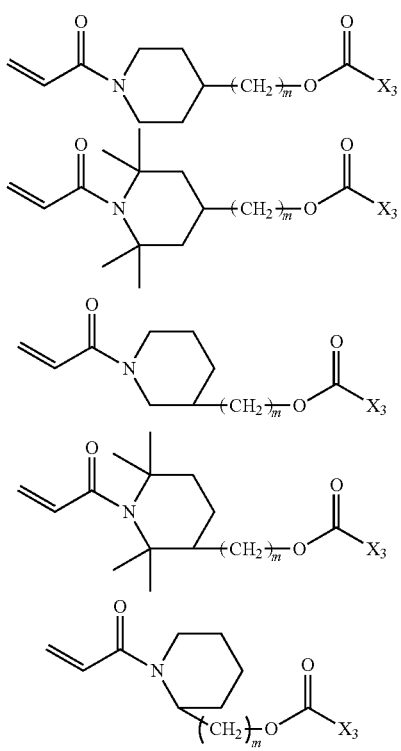

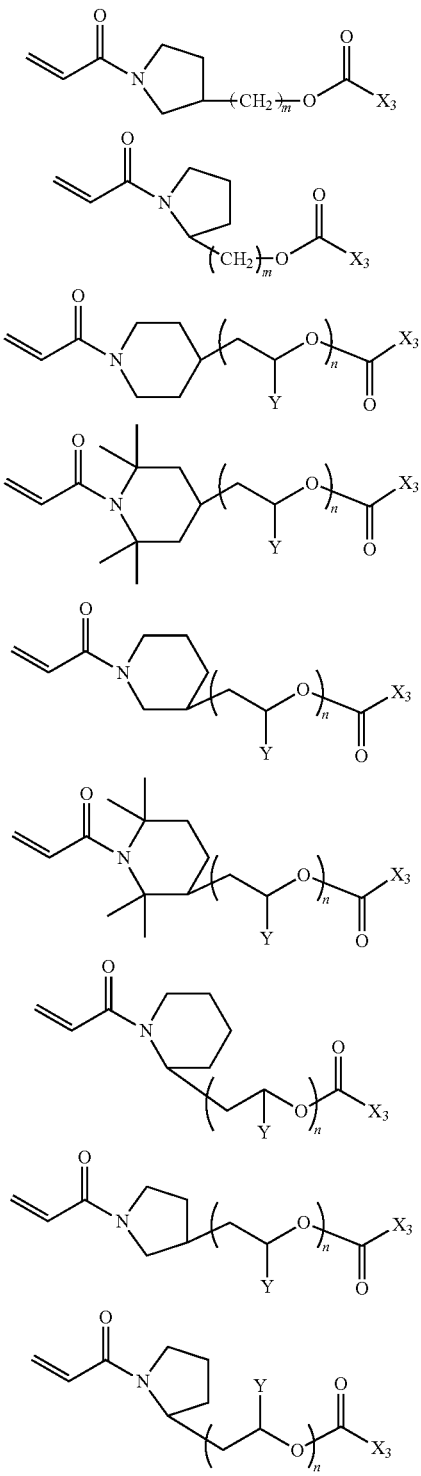

In the compound represented by chemical formula 4, there is no specific limit to the compound having an alkyl group having 1 to 10 carbon atoms as R$_6$. Specific examples thereof include, but are not limited to, compounds represented by the following chemical formulae (where m represents 0 or an integer of from 1 to 6).

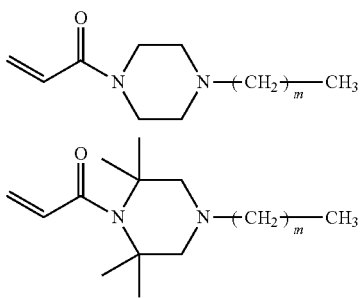

In the compound represented by chemical formula 4, there is no specific limit to the compound independently having monovalent groups containing groups represented by —NX$_4$X$_5$ (where X$_4$ and X$_5$ each, independently represent monovalent hydrocarbon groups having 1 to 10 carbon atoms) as R$_6$. Specific examples thereof include, but are not limited to, compounds represented by the following chemical formulae (where m represents 0 or an integer of from 1 to 6).

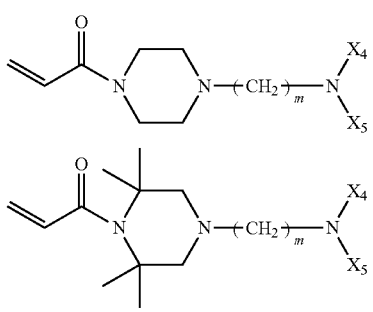

In the compound represented by chemical formula 4, there is no specific limit to the compound having a monovalent group containing a group represented by —OX$_1$ (where X$_1$ represents a monovalent hydrocarbon group having 1 to 10 carbon atoms) as R$_6$. Specific examples thereof include, but are not limited to, compounds represented by the following chemical formulae (where Y is a hydrogen atom or a methyl group, n is an integer of from 1 to 4, and m represents 0 or an integer of from 1 to 6).

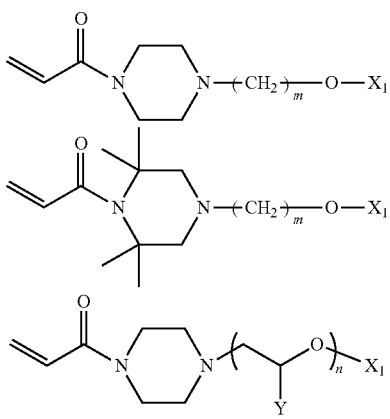

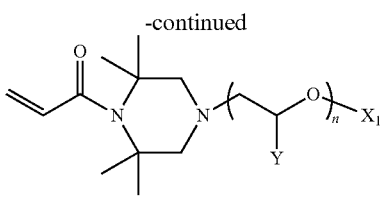

In the compound represented by chemical formula 4, there is no specific limit to the compound having a monovalent group containing a group represented by —COOX$_2$ (where X$_2$ represents a monovalent hydrocarbon group having 1 to 10 carbon atoms) as R$_6$. Specific examples thereof include, but are not limited to, compounds represented by the following chemical formulae (where m represents 0 or an integer of from 1 to 6).

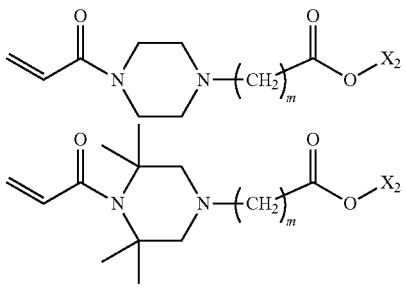

In the compound represented by chemical formula 4, there is no specific limit to the compound having a monovalent group containing a group represented by —OCOX$_3$ (where X$_3$ represents a monovalent hydrocarbon group having 1 to 10 carbon atoms) as R$_6$. Specific examples thereof include, but are not limited to, compounds represented by the following chemical formulae (where Y is a hydrogen atom or a methyl group, n is an integer of from 1 to 4, and m represents 0 or an integer of from 1 to 6).

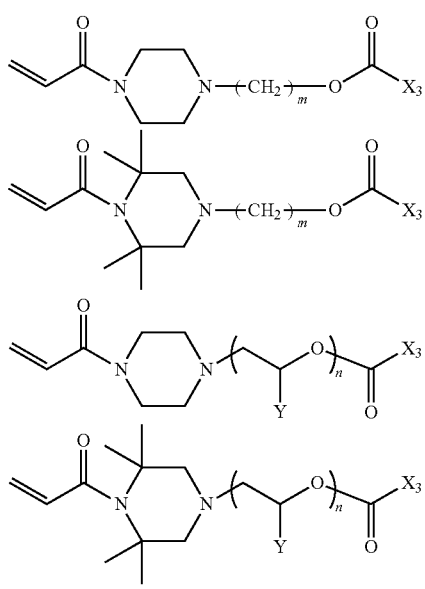

The compound represented by chemical formula 1, 2, 3, or 4 has a viscosity of 100 mPa·s or less at 25° C. and, preferably, 50 mPa·s or less.

The ink of the present disclosure may contain two or more kinds of the compounds represented by chemical formula 1, 2, 3, or 4.

The total content of the compound represented by chemical formula 1, 2, 3, or 4 in the ink ranges from 20% by weight to 98% by weight, preferably from 30% by weight to 90% by weight, and more preferably from 30% by weight to 80% by weight.

It is preferable that the ink contains a photopolymerization initiator.

Specific examples of the photopolymerization initiator include, but are not limited to, a photoradical polymerization initiator, a photocation polymerization initiator (photoacid producing agent), and a photoanion polymerization initiator (photobase producing agent). These can be used alone or in combination. Of these, photoradical polymerization initiators and photoanion polymerization initiators are preferable.

The photopolymerization initiator is a compound producing a polymerization initiating species by absorbing an active energy ray.

There is no specific limit to the active energy ray. Specific examples thereof include, but are not limited to, gamma ray, beta ray, an electron beam, an ultraviolet ray, visible light, and an infrared ray.

There is no specific limit to the photopolymerization initiator. Specific examples thereof include, but are not limited to, aromatic ketones, acyl phosphine oxide compounds, aromatic onium salt compounds, organic peroxides, thio compounds, hexaaryl biimidazol compounds, ketoxim ester compounds, borate compounds, adinium compounds, metallocene compounds, active ester compounds, compounds having carbon halogen bonds, and alkyl amine compounds.

Specific examples of photoradical polymerization initiators include, but are not limited to, benzophenone, Michler's ketone, 4,4'-bis(diethylamino)benzophenone, xanthone, thioxanthone, isopropyl xanthone, 2,4-diethylthio xanthone, 2-ethyl anthraquinone, acetophenone, 2-hydroxy-2-methyl propiophenone, 2-hydroxy-2-methyl-4'-isopropyl propiophenone, 1-hydroxy cyclohexyl phenyl keton, isopropyl benzoin ether, isobutyl benzoin ether, 2,2-diethoxy acetophenone, 2,2-dimethoxy-2-phenylacetophenone, Camphorquinone, benzanthrone, 2-methyl-1-[4-(methylthio)phenyl]-2-morpholinopropane-1-one, 2-benzyl-2-dimethylamino-1-(4-morpholinophenyl)butanone-1,4-dimethylamino ethyl benzoate, 4-dimethylamino isoamyl benzoate, 4,4'-bis(t-butylperoxycarbonyl)benzophenone, 3,4,4'-tris(t-butylperoxycarbonyl)benzophenone, 3,3',4,4'-tetra(t-butylperoxycarbonyl)benzophenone, 3,3',4,4'-tetra(t-hexylperoxycarbonyl)benzophenone, 3,3'-bis(methoxycarbonyl)-4,4'-bis(t-butylperoxycarbonyl)benzophenone, 3,4'-bis(methoxycarbonyl)-4,3'-bis(t-butylperoxycarbonyl) benzophenone, 4,4'-bis(methoxycarbonyl)-3,3'-bis(t-butylperoxycarbonyl)benzophenone, 1,2-octane dione, 1-[4-(phenylthio)phenyl]-2-(o-benzoyloxime), 2-(4'-methoxystyryl)-4,6-bis(trichloromethyl)-s-triadine, 2-(3',4'-dimethoxystyryl)-4,6-bis(trichloromethyl)-s-triadine, 2-(2',4'-dimethoxystyryl)-4,6-bis(trichloromethyl)-s-triadine, 2-(2'-methoxystyryl)-4,6-bis(trichloromethyl)-s-triadine, 2-(4'-pentyloxystyryl)-4,6-bis(trichloromethyl)-s-triadine, 4-[p-N,N-bis(ethoxycarbonylmethyl)-2,6-bis(trichloromethyl)-s-triadine, 1,3-bis(trichloromethyl)-5-(2'-chlorophenyl)-s-triadine, 1,3-bis(trichloromethyl)-5-(4'-methoxyphenyl)-s-triadine, 2-(p-dimethylaminostyryl)benzoxazole, 2-(p-dimethylaminostyryl)benzthiazole, 2-mercaptobenzthiazole, 3,3'-carbonylbis(7-diethylamino coumarin), 2-(o-chlorophenyl)-4,4',5,5'-tetraphenyl-1,2'-biimidazole, 2,2'-bis(2-chlorophenyl)-4,4',5,5'-tetrakis(4-ethoxycarbonylphenyl)-1,2'-biimidazole, 2,2'-bis(2,4-dichlorophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-trichlorophenyl)-4,4',5,5'-tetraphenyl-1,2'-biimidazole, 3-(2-methyl-2-dimethylaminopropionyl)carbazole, 3,6-bis(2-methyl-2-morpholinopropionyl)-9-n-dodecyl carbazole, 1-hydroxy cyclohexyl phenylketone, bis(η5-2,4-cyclopentadiene-1-yl)-bis[2,6-difluoro-3-(1-H-pyrrol-1-yl)phenyl]titanium, bis (2,4,6-trimethylbenzoyl)phenyl phosphine oxide, and 2,4,6-trimethylbenzoyl)diphenyl phosphine oxide.

Of these, bis(2,4,6-trimethylbenzoyl)phenyl phosphine oxide (IRGACURE 819, manufactured by BASF Japan), 2,4,6-trimethylbenzoyl)diphenyl phosphine oxide (DAROCUR TPO, manufactured by BASF Japan), 1-hydroxycylohexyl phenyl ketone (IRGACURE 184, manufactured by BASF Japan), 2-methyl-1-[4-(methylthio)phenyl]-2-morpholinopropane-1-one (IRGACURE 907, manufactured by BASF Japan), and 2-dimethylamino-2-(4-methylbenzyl)-1-(4-morpholine-4-ylphenyl)butane-1-one (IRGACURE 379, manufactured by BASF Japan) are preferable because these are highly soluble in other components contained in ink and the ink can be cured by exposure to a small amount of ultraviolet ray.

The mass ratio of the photopolymerization initiator to the total amount of the compound represented by chemical formula 1, 2, 3, or 4 and the coloring agent ranges from 0.01 to 0.50, preferably from 0.02 to 0.40, and more preferably from 0.05 to 0.30.

The ink of the present disclosure optionally contains a coloring agent. By the coloring agent, a colored image can be formed.

There is no specific limit to the coloring agent. Specific examples of the coloring agent include, but are not limited to, pigments, oil-soluble dyes, hydrosoluble dyes, and disperse dyes. These can be used alone or in combination.

Of these, pigments and oil-soluble dyes are preferable and of the two, pigments are more preferable because these are tough to environment change.

It is preferable that the coloring agent does not serve as polymerization inhibitor in order not to have an adverse impact on the sensitivity of photopolymerization reaction by active energy ray.

Specific examples of red pigments or magenta pigments include, but are not limited to, Pigment Red 3, 5, 19, 22, 31, 38, 43, 48:1, 48:2, 48:3, 48:4, 48:5, 49:1, 53:1, 57:1, 57:2, 58:4, 63:1, 81, 81:1, 81:2, 81:3, 81:4, 88, 104, 108, 112, 122, 123, 144, 146, 149, 166, 168, 169, 170, 177, 178, 179, 184, 185, 208, 216, 226, and 257, Pigment Violet 3, 19, 23, 29, 30, 37, 50, and 88, and Pigment Orange 13, 16, 20, and 36.

Specific examples of blue pigments or cyan pigments include, but are not limited to, Pigment Blue 1, 15, 15:1, 15:2, 15:3, 15:4, 15:6, 16, 17-1, 22, 27, 28, 29, 36, and 60.

Specific examples of green pigments include, but are not limited to, Pigment Green 7, 26, 36, and 50.

Specific examples of yellow pigments include, but are not limited to, Pigment Yellow 1, 3, 12, 13, 14, 17, 34, 35, 37, 55, 74, 81, 83, 93, 94, 95, 97, 108, 109, 110, 137, 138, 139, 153, 154, 155, 157, 166, 167, 168, 180, 185, and 193.

Specific examples of black pigments include, but are not limited to, Pigment Black 7, 28, and 26.

Specific examples of white pigments include, but are not limited to, Pigment White 6, 18, and 21.

Specific examples of the oil-soluble yellow dyes include, but are not limited to, an aryl or heteryl azo dye having a phenolic compound, a naphthol compound, an aniline compound, a pyrazolone compound, a pyridone compound, or a compound having an open chain active methylene compound as coupling component, a methine dye such as an azomethine, a benzylidene dye, or a monomethine oxonol having an open chain active methylene compound as coupling component, a quinone dye such as a naphthoquinone dye and an anthraquinone dye, a quinophthalone dye, a nitro•nitroso dye, an acrylidine dye, and an acrydinone dye.

Specific examples of the oil-soluble magenta dyes include, but are not limited to, an aryl or heteryl azo dye having a phenolic compound, a naphthol compound, or an aniline compound as coupling component, a methine dye such as an azomethine dye, an arylidene dye, a styryl dye, a merocyanine dye, or an oxonol dye having a pyrazolone or a pyridone as coupling component, a carbonium dye such as diphenyl methane dye, a triphenyl methane dye, and a xanthene dye, a quinone dye such as a naphthoquinone dye, an anthraquinone dye, and an anthrapyridone dye, and a condensed polycyclic dye such as a dioxadine dye.

Specific examples of the oil-soluble cyan dyes include, but are not limited to, an indoaniline dye, an indophenol dye, a polymethine dye such as azomethine dye, cyanine dye, oxonol dye, and merocycnine dye having a pyrrolo triazole as coupling component, a carbonium dye such as diphenyl methane dye, a triphenyl methane dye, and a xanthene dye, a phthalocyanine dye, an anthraquinone dye, an aryl or heteryl azo dye having a phenolic compound, a naphthol compound, or an aniline compound as coupling component, and indigo•thioindigo dye.

Specific examples of the oil-soluble dyes include, but are not limited to, C.I. Solvent Black 3, 7, 27, 29, and 34, C.I. Solvent Yellow 14, 16, 19, 29, 30, 56, 82, 93, and 162, C.I. Solvent Red 1, 3, 8, 18, 24, 27, 43, 49, 51, 72, 73, 109, 122, 132, and 218; C.I. Solvent Violet 3; C.I. Solvent Blue 2, 11, 25, 35, 38, 67, and 70; C.I. Solvent Green 3 and 7, and C.I. Solvent Orange 2.

Specific examples of the disperse dyes include, but are not limited to, C.I. Disperse Yellow 5, 42, 54, 64, 79, 82, 83, 93, 99, 100, 119, 122, 124, 126, 160, 184:1, 186, 198, 199, 201, 204, 224, and 237 C.I. Disperse Orange 13, 29, 31:1, 33, 49, 54, 55, 66, 73, 118, 119, and 63; C.I. Disperse Red 54, 60, 72, 73, 86, 88, 91, 92, 93, 111, 126, 127, 134, 135, 143, 145, 152, 153, 154, 159, 164, 167:1, 177, 181, 204, 206, 207, 221, 239, 240, 258, 277, 278, 283, 311, 323, 343, 348, 356, and 362; C.I. Disperse Violet 33, C.I. Disperse Blue, 60, 73, 87, 113, 128, 143, 148, 154, 158, 165, 165:1, 165:2, 176, 183, 185, 197, 198, 201, 214, 224, 225, 257, 266, 267, 287, 354, 358, 365, and 368, and C.I. Disperse Green 6:1 and 9.

It is preferable that such pigments is moderately dispersed in ink

There is no specific limit to a dispersion device to disperse a pigment. Specific examples thereof include, but are not limited to, a ball mill, a sand mill, a ring mill, an attritor, a roll mill, an aditator, a HENSCHEL MIXER, a colloid mill, an ultrasonic homogenizer, a pearl mill, a wet-type jet mill, and a paint shaker.

It is possible to add a dispersing agent when dispersing a pigment.

There is no specific limit to such a dispersing agent. A polymer dispersing agent is preferable.

The mass ratio of a dispersing agent to a pigment ranges from 0.01 to 0.50.

The average particle diameter of the pigment in ink ranges from 0.005 μm to 0.5 μm, preferably from 0.01 μm to 0.45 μm, and more preferably from 0.015 μm to 0.4 μm.

When the average particle diameter is within such a range, it is possible to suppress clogging of the nozzle of an ink jet head and maintain the preservation stability, the transparency, and the photocurability of ink.

The content of the coloring agent in ink ranges from 0.5% by weight to 10% by weight and preferably from 1% by weight to 8% by weight.

The content of the coloring agent in white ink having a white pigment formed of titanium oxide as coloring agent ranges from 5% by weight to 30% by weight and preferably from 10% by weight to 25% by weight. When the content is within such a range, it is possible to maintain the shielding property of ink.

The ink of the present disclosure may include a photopolymerizable compound other than the compound represented by chemical formula 1, 2, 3, or 4.

The mass ratio of the photopolymerizable compound other than the compound represented by chemical formula 1, 2, 3, or 4 to the compound represented by chemical formula 1, 2, 3, or 4 ranges from 0.01 to 100 and preferably from 0.1 to 50.

There is no specific limit to the photopolymerizable compound other than the compound represented by chemical formula 1, 2, 3, or 4. Specific examples thereof include, but are not limited to, a photoradical polymerizable compound, a photocation polymerizable compound, a photoanion polymerizable compound. These can be used alone or in combination.

As the photoradical polymerizable compound, any compound that has at least one ethylene-based unsaturated group capable of photoradical polymerization is suitable for use. These include, monomers, oligomers, polymers, etc.

The photoradical polymerizable compound include, but are not limited to, unsaturated carboxylic acids such as acrylic acid, methacrylic acid, itaconic acid, crotonic acid, isocrotonic acid, and maleic acid, salts thereof, and compounds derived therefrom, anhydrides having ethylene-based unsaturated groups, acrylonitrile, styrene, unsaturated polyesters, unsaturated polyethers, unsaturated polyamides, and unsaturated urethanes.

Specific examples of the photoradical polymerizable compound include, but are not limited to derivatives of acrylic acid such as 2-hydroxyethyl acrylate, butoxyethyl acrylate, carbitol acrylate, cyclohecyl acrylate, tetrahydrofurfuryl acrylate, benzyl acrylate, bis(4-acryloxy polyethoxyphenyl)propane, neopentyl glycol diacrylate, ethoxified neopentyl glycol diacrylate, propoxynated neopentyl glycol diacrylate, 1,6-hexane diol diacrylate, ethylene glycol diacrylate, diethylene glycol diacrylate, triethylene glycol diacrylate, tetraethylene glycol diacrylate, polyethylene glycol diacrylate, propylene glycol diacrylate, dipropylene glycol diacrylate, tripropylene glycol diacrylate, tetrapylene glycol diacrylate, polypropylene glycol diacrylate, pentaerythriol triacrylate, pentaerythriol tetraacrylate, dipentaerythriol tetraacrylate, trimethylol propane triacrylate, tetramethylol methane tetraacrylate, oligoester acrylate, and epoxyacrylate; derivatives of methacrylic acid such as methyl methacrylate, n-butyl methacrylate, allyl methacrylate, glycidyl methacrylate, benzyl methacrylate, dimethylaminomethyl methacrylate, 1,6-hexane diol dimethacrylate, ethylene glycol dimethacrylate, triethylene glycol dimethacrylate, polyethylene glycol dimethacrylate, polypropylene glycol dimethacrylate, trimethylol ethane trimethacrylate, trimethytlol propane trimethacrylate, and 2,2-bis(4-methacryloxy polyethoxy phenyl)propane; derivatives of acrylic amide such as N-methylol acrylic amide, diacetone acrylic amide, 2-hydroxyethyl acrylic amide, and acryloyl morpholine; derivatives of allyl compounds such as allyl glycidyl ether, diallyl phthalate, and triallyl trimellitate, di- or trivinyl ether compounds such as ethylene glycol divinyl ether, ethylene glycol monovinyl ether, diethylene glycol divinyl ether, triethylene glycol monovinyl ether, triethylene glycol divinyl ether, propylene glycol divinyl ether, dipropylene glycol divinyl ether, butane diol divinyl ether, hexane diol divinyl ether, cyclohexane dimethanol divinyl ether, hydroxyethyl monovinyl ether, hydroxynonyl monovinyl ether, and trimethylol propane trivinyl ether; monovinylether compounds such as ethylvinylether, n-butylvinylether, isobutylvinylether, octadecylvinylether, cyclohexylvinylether, hydroxybutylvinylether, 2-ethylhexylvinylether, cyclohexanedimethanol monovinylether, n-propyl vinylether, idopropyl vinylether, isopropenyl ether-o-propylene carbonate, dodecyl vinylether, diethylene glycol monovinylether, and octadecylvinylether; 2-ethylhexyl diglycol acrylate, 2-hydroxy-3-phenoxypropyl acrylate, 2-hydroxybutylacrylate, hydroxy pivalic acid neopentyl glycol diacrylate, 2-acryloyloxy ethyl phthalic acid, methoxy polyethylene glycol acrylate, tetramethylol methane triacrylate, 2-acryloyloxy ethyl-2-hydroxy ethyl phthalic acid, dimethylol tricyclodecane diacrylate, ethoxified phenyl acrylate, 2-acryloyloxy ethyl succinic acid, an acrylate of an adduct of nonyl phenol with ethylene oxide, a modified glycerine acrylate, an adduct of bisphenol A with diglycidyl ether acrylic acid, a modified bisphenol A diacrylate, a phenoxy-polyethylene glycol acrylate, 2-acryloyloxyethyl hexahydrophthalic acid, a diacrylate of an adduct of bisphenol A with propylene oxide, a diacrylate of an adduct of bisphenol A with ethylene oxide, dipentaerythritol hexaacrylate, pentaerythritol triacrylate, tolylene diisocyanate urethane prepolymer, lactone-modified flexible acrylate, buthoxyethyl acrylate, an adduct of propylene glycol with diglycidyl ether acrylic acid, pentaerythritol triacrylate, hexamethylene diisocyanate urethane prepolymer, 2-hydroxyethyl acrylate, methoxy dipropylene glycol acrylate, ditrimethylol propane tetraacrylate, pentaerythritol triacrylate, hexamethylene diisocyanate urethane prepolymer, stearyl acrylate, isoamylacrylate, isomyristyl acrylate, isostearyl acrylate, and lactone-modified acrylate.

As the combination of the photopolymerizable compound and the photopolymerization initiator, in addition to the combination of the photoradical polymerizable compound and the photoradical polymerization initiator, a combinational use of a photocation polymerizable compound and a photocation polymerization initiator and a combinational use of a photoanion photopolymerizable compound and a photoanion polymerization initiator are also suitable.

Specific examples of the photocation polymerizable compounds include, but are not limited to, epoxy compounds, vinylether compounds, and oxetane compounds.

Specific examples of the photocation polymerization initiator include, but are not limited to, salts of $B(C_6F_5)_4^-$, $PF_5^-$, $ASF_6^-$, $SbF_6^-$, and $CF_3SO_3^-$ of aromatic onium compounds of diazonium, ammonium, iodonium, sulphonium, and phosphonium, sulphone compounds capable of producing sulfonic acid, halogenated compounds capable of producing halogenated hydrogen, and iron allene complexes.

Specific examples of the photoanion polymerizable compounds include, but are not limited to, epoxy compounds, lactone compounds, acrylic compounds, and methacrylic compounds. Of these, the acrylic compounds and methacrylic compounds specified as preferable photoradical polymerizable compounds are preferable.

Specific examples of photoanion polymerization initiator include, but are not limited to, o-nitrobenzyl carbamate derivatives, o-acyloxy derivatives, and o-carbamoyloxime amidine.

The ink of the present disclosure optionally contains a sensitizer to promote decomposition of a photopolymerization initiator upon exposure to active energy ray.

A sensitizer is excited by absorbing active energy ray. When the sensitizer in the excited state contacts a polymerization initiator, chemical change of the polymerization initiator is promoted by electron transfer, energy transfer, heat, etc.

There is no specific limit to the sensitizer. For example, a sensitizing pigment having an absorption wavelength in a range of from 350 nm to 450 nm is suitable.

Specific examples of the sensitizing pigment having an absorption wavelength in a range of from 350 nm to 450 nm include, but are not limited to, multi-nuclear aromatic compounds (such as pyrene, perylene, and triphenylene), xanthenes (such as flourescein, eosin, Erythrosin, Rhodamine B, and rose bengal), cyanines (such as thiacarbocyanine and oxacarbocyanine), merocyanines (such as merocyanine and carbomerocyanine), thiazines (such as thionine, methylene blue, and toluidine blue), acridines (such as acridine orange, chloroflavin, and acriflavin), anthraquinones (such as anthraquinone), squarylium (such as squarylium), and coumalins (such as 7-diethylamino-4-methyl coumalin).

The mass ratio of this sensitizing pigment to a photopolymerization initiator ranges from $5\times10^{-3}$ to 200 and preferably from 0.02 to 50.

The link of the present disclosure optionally contains a co-sensitizer.

Co-sensitizers enhances the sensitivity of sensitizing pigments to active energy ray or subdues polymerization inhibition of photopolymerizable compounds by oxygen.

There is no specific limit to such co-sensitizers. Specific examples thereof include, but are not limited to, amine-based compounds such as triethanol amines, p-dimethyl amino benzoic acid ethyl esters, p-formyl dimethylaniline and p-methylthio dimethylaniline, thiols such as 2-mercapto benzothiazole, 2-mercaptobenzooxazole, 2-mercapto benzoimidazole, 2-mercapto-4(3H)-quinazoline, and β-mercapto naphthalene, and sulfides.

The ink of the present disclosure may contain a polymerization inhibitor. The preservation stability of ink is improved by a polymerization inhibitor. In addition, it is possible to prevent clogging of the nozzle of an ink jet head due to thermal polymerization when ink is heated to decrease the viscosity thereof before discharging.

There is no specific limit to the polymerization inhibitor. Specific examples thereof include, but are not limited to, hydroquinone, benzoquinone, p-methoxyphenol, TEMPO, TEMPOL, and a cupferron complex of aluminum.

The content of a polymerization inhibitor in ink ranges from 200 ppm to 20,000 ppm The viscosity of ink ranges from 7 mPa·s to 30 mPa·s and preferably from 7 mPa·s to 25 mPa·s taking into account the discharging properties of the ink in an ink jet device.

Since the ink of the present disclosure is of an active energy ray curing type, it is preferable that it does not contain a solvent. However, to improve the attachability between the ink after curing and a recording medium, it may further contain a solvent more unless the curing speed of the ink is not affected.

There is no specific limit to the selection of solvent. Examples thereof are, organic solvents and water.

The content of an organic solvent in ink is from 0.1% by weight to 5% by weight and preferably from 0.1% by weight to 3% by weight.

Furthermore, the ink optionally contains a surfactant, a leveling additive, a matte agent, and resins such as polyester resins, polyurethane resins, vinyl resins, acrylic resins, rubber resins, and wax resins to adjust film properties.

In addition, the ink optionally contains a tackifier having no polymerization inhibition effect to improve the attachability of the ink to polyolefin, PET, etc.

The ink of the present disclosure can be accommodated in a container in an ink cartridge. If ink is used in an ink cartridge, a user does not touch the ink directly in operations such as ink replacement, thereby avoiding contamination of hands, fingers and clothes. Also, it is possible to prevent mingling of foreign objects such as rubbish into ink.

There is no specific limit to the selection of the container, for example, ink bags formed of materials with no air permeability such as aluminum laminate film or resin film are suitable.

FIG. 1 is a diagram illustrating an example of the ink cartridge according to an embodiment of the present invention.

An ink bag 11 has an ink inlet 12 and an ink outlet 13. The ink bag 11 is filled with ink through the ink inlet 12. Subsequent to evacuation of air remaining in the ink bag 11, the ink inlet 12 is sealed by fusion. When using the ink bag 11, the ink outlet 13 is pierced with a needle formed on an ink jet recording device to supply the ink to the ink jet recording device. The ink outlet 13 is formed of a rubber material.

The ink bag 11 is accommodated in a cartridge housing 14 made of plastic, which is detachably attached to the ink jet recording device as the ink cartridge 10. Since the ink cartridge 10 is detachably attachable to the ink jet recording device, it is possible to improve the working efficiency of supplement or replacement of ink.

The ink jet recording device of the present disclosure has the ink cartridge and an ink discharging head to discharge ink for recording.

There is no specific limit to the ink discharging method, for example, a continuous spraying method and an on-demand method are useful.

The on-demand method employs a piezo system, a thermal system, or an electrostatic system.

Figure 2:
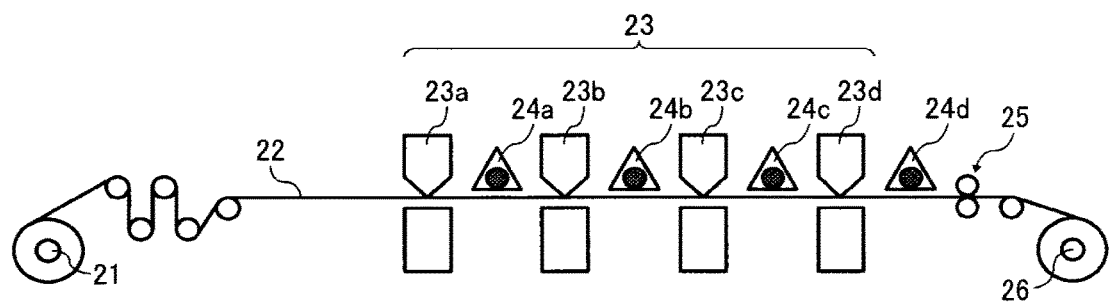
FIG. 2 is a diagram illustrating a printing mechanism of an ink jet recording device to describe the entire configuration of the ink jet recording device.

The printing mechanism of the ink jet recording device is described with reference to FIG. 2.

Due to printing units 23a, 23b, 23c, and 23d of colors of yellow, magenta, cyan, and black, ink is discharged to a print substrate 22 fed from a print substrate supplying roll 21. The ink is separately discharged per color of yellow, magenta, cyan, and black. Thereafter, the ink is exposed to ultraviolet ray emitted from light sources 24a, 24b, 24c, and 24d to photocure the ink, so that a color image is formed. Thereafter, the print substrate 22 is transferred to a process unit 25 and a printed matter roll-up roll 26.

A heating unit is optionally provided to each of the printing units 23a, 23b, 23c, and 23d at the ink discharging portion to liquidize ink.

The temperature of the print substrate may rise when the printed area of the previous color is large or the transfer speed of the print substrate is high. For this reason, a mechanism of cooling down a print substrate to around room temperature is provided in a contact or non-contact manner as an option.

There is no specific limit to the print substrate 22, typically paper, film, metal, or mixtures thereof.

The print substrate 22 may have a sheet-like form.

In addition, it is possible to have an installation for simplex printing and duplex printing.

Furthermore, it is possible to irradiate the print substrate with ultraviolet ray emitted from the light source 24d while exposure to ultraviolet ray from the light sources 24a, 24b, and 24c is weakened or omitted. This contributes to energy-saving and cost efficiency.

A composition that contains the compound represented by chemical formula 1, 2, 3, or 4 can be used as adhesive or applicable to form solid objects.

Having generally described preferred embodiments of this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Next, the present disclosure is described in detail with reference to Examples and Comparative examples but not limited thereto.

$^1$H-NMR spectrum was monitored by using a $^1$H-NMR (500 MHz) (manufactured by JEOL Ltd.). FT-IR Spectrum GX (manufactured by PerkinElmer Co., Ltd.) was used for IR spectrum. Mass spectrum was monitored by LCT Premer XE (manufactured by MICROMASS TECHNOLOGIES).

Example 1

8.0 g (90 mmol) of N-2-(methoxyethyl)methyl amine was added to 100 ml of dehydrated dichlormethane in a flask followed by Ar gas replacement. Thereafter, 13.4 g (132 mmol) of triethyl amine was added thereto. Next, the system was cooled down to about −10° C. 10.0 g (110 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 5.8 g (yield: about 45%) of an oily, pale yellow material represented by the following chemical formula.

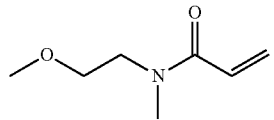

(1-1)

$^1$H-NMR (CDCl$_3$):δ3.04(s,1.5H),3.15(s,1.5H),3.35(s,3H) 3.49-3.64(m,4H)5.63-5.71(m,1H),6.28-6.35(m,1H),6.56-6.66(m,1H)

IR(NaCl):2982,2932,2892,2830,1651,1613,1450,1417, 1404,1359,1282,1192,1117,1060, 1018,982,958,826,795, 747,607,536cm$^{-1}$

Example 2

8.0 g (60 mmol) of bis(methoxyethyl) amine was added to 100 ml of dehydrated dichlormethane in a flask followed by Ar gas replacement. Thereafter, 8.8 g (87 mmol) of triethyl amine was added thereto. Next, the system was cooled down to about −10° C. 6.5 g (72 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material.

Furthermore, by a column chromatography filled with 300 g of Wakogel C300 (manufactured by Wako Pure Chemical Industries, Ltd.) using hexane and ethyl acetate as eluate, the oily brown material was fined to obtain 5.5 g (yield: about 50%) of an oily, pale yellow material represented by the following chemical formula.

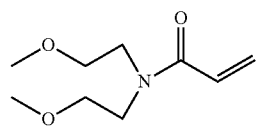

(2-1)

$^1$H-NMR (CDCl$_3$):δ3.34(d,6H),3.51(t,2H),3.57(t,2H), 3.63(t,4H),5.67(dd,1H), 6.34(dd,1H),6.64-6.69(m,1H)

IR(NaCl):2982,2930,2981,2829,1651,1613,1447,1366, 1315,1270,1230,1193,1157,1118, 1069,1015,981,962,824, 795,529cm$^{-1}$

Example 3

9.7 g (60 mmol) of bis(ethoxyethyl) amine was added to 100 ml of dehydrated dichloromethane in a flask followed by Ar gas replacement. Thereafter, 8.8 g (87 mmol) of triethyl amine was added thereto. Next, the system was cooled down to about −10° C. 6.5 g (72 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, 6.5 g (yield: about 50%) of an oily, pale yellow material represented by the following chemical formula was obtained.

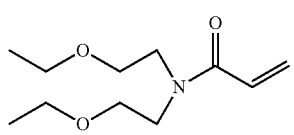

(2-2)

$^1$H-NMR(CDCl$_3$):δ1.18(t,6H),3.48(q,4H),3.55(t,2H), 3.59-3.66(m,6H),5.67(dd,1H), 6.33(dd,1H),6.65-6.72(m,1H)

IR(NaCl):2976,2933,2868,1651,1614,1471,1445,1373, 1353,1317,1277,1225,1118,980, 795,522cm$^{-1}$

Example 4

8.3 g (70 mmol) of methylamino acetoaldehyde dimethyl acetal was added to 100 ml of dehydrated dichlormethane in a flask followed by Ar gas replacement. Thereafter, 10.1 g (100 mmol) of triethyl amine was added thereto. Next, the system was cooled down to about −10° C. 7.6 g (84 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 7.3 g (yield: about 60%) of an oily, pale yellow material represented by the following chemical formula.

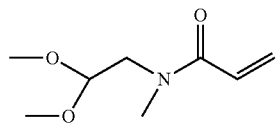

(1-2)

$^1$H-NMR(CDCl$_3$):δ3.06(s,1H),3.15(s,2H),3.42(d,6H), 3.50(dd,2H), 4.42(t,0.35H),4.54(t,0.65H),5.64-5.74(m,1H), 6.30-6.38(m,1H),6.57-6.69(m,1H)

IR(NaCl):2941,2835,1652,1614,1452,1417,1378,1308, 1276,1240,1190,1123,1075,982, 919,819,796,544cm$^{-1}$

Example 5

9.5 g (50 mmol) of imino diethyl diacetate was added to 100 ml of dehydrated dichlormethane in a flask followed by Ar gas replacement. Thereafter, 7.3 g (72 mmol) of triethyl amine was added thereto. Next, the system was cooled down to about −10° C. 5.4 g (60 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 7.5 g (yield: about 62%) of an oily, pale yellow material represented by the following chemical formula.

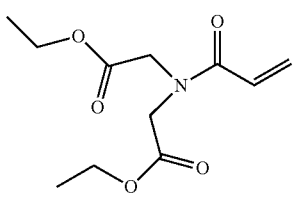

(2-3)

¹H-NMR(CDCl₃):δ1.21(t,6H),4.10-4.19(m,8H),5.69(dd,1H),6.28(dd,1H),6.36-6.43(m,1H)

IR(NaCl):2985,2941,2909,1747,1659,1621,1462,1409,1374,1352,1295,1259,1193,1097, 1070,1026,972,869,796,734,641,558cm⁻¹

Example 6

15.0 g (200 mmol) of 2-methylamino)ethanol was added to 200 ml of dehydrated dichloromethane in a flask followed by Ar gas replacement. Thereafter, 24.3 g (240 mmol) of triethyl amine was added thereto. Next, the system was cooled down to about −10° C. 18.1 g (200 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 7.9 g (yield: about 30%) of an oily, transparent material represented by the following chemical formula.

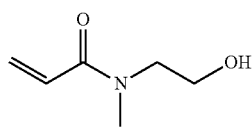

(1-3)

¹H-NMR(CDCl₃):δ3.02(s,1.5H),3.15(s,1.5H),3.52(t,1H),3.60(t,1H),3.73-3.83(m,2H),5.62-5.75(m,1H),6.23-6.34(m,1H),6.55-6.74(m,1H)

IR(NaCl):3391,2937,2879,1645,1606,1486,1452,1420,1406,1359,1259,1211,1116,1052, 981,862,796,748,609cm⁻¹

Example 7

140 ml of dehydrated tetrahydrofuran was added to 6.1 g (140 mmol) of sodium hydride in a flask followed by Ar gas replacement. Thereafter, a solution in which 14.3 g (100 mmol) of 2-(cyclohexylamino)ethanol was dissolved in 50 ml of tetrahydrofuran was slowly dropped in the flask at room temperature and the system was stirred for 24 hours at room temperature. Next, after 21.8 g (140 mmol) of ethyl iodide was slowly added while being cooled in water, the system was stirred at room temperature for 24 hours. Furthermore, after filtration, the filtrate was condensed. Next, 100 ml of ethyl acetate was added to the system, the resultant was washed with water. Furthermore, subsequent to drying by sodium sulfate, the dried resultant was condensed under a reduced pressure to obtain 14.7 g (yield: about 86%) of an oily orange material represented by the following chemical formula.

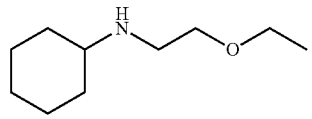

¹H-NMR(CDCl₃):δ0.80-0.90(m,1H),1.00-1.30(m,8H),1.62(d,1H),1.73(d,2H), 1.88(d,2H),2.38-2.45(m,1H),2.80(t,2H),3.49(t,2H),3.55(t,2H)

IR(NaCl):2974,2927,2854,1449,1378,1348,1260,1228,1115,890,835,760,533cm⁻¹ 7.7 g (45 mmol) of the oily orange material was added to 100 ml of dehydrated dichlormethane in a flask followed by Ar gas replacement. Thereafter, 6.6 g (65 mmol) of triethyl amine was added thereto. Next, the system was cooled down to about −10° C. 4.9 g (54 mmol) of acrylic acid chloride was slowly dropped in the system while keeping the temperature in the system ranged from −10° C. to −5° C. and thereafter stirred at a room temperature for two hours. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 5.1 g (yield: about 50%) of an oily, pale yellow material represented by the following chemical formula.

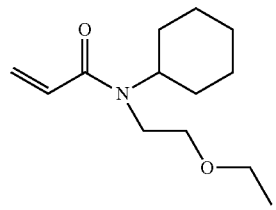

(1-4)

¹H-NMR(CDCl₃):δ1.11(qd 1H),1.17-1.23(d 3H),1.25-1.48(m,3H),1.55(q,1H),1.62-1.89(m,5H),3.40-3.60(m,6H),3.66(t,1H),5.66(t,1H),6.23-6.38(dd,1H),6.55-6.69(m,1H)

IR(NaCl):2974,2931,2857,1650,1611,1468,1427,1351,1301,1261,1238,1147,1115,1058, 980,895,795cm⁻¹

Example 8

After 11.8 g (60 mmol) of pentacarbonyl iron was added to 360 ml of 0.5 N ethanol solution of potassium hydroxide at a room temperature, 5.4 g (60 mmol) of 2-ethoxyethyl amine and 6.4 g (60 mmol) of benzaldehyde were further added at a room temperature followed by stirring for 24 hours. Next, the system was stirred for three hours at about 50° C. followed by filtration. Furthermore, after concentration of the filtrate, 100 ml of ethyl acetate was added. Next, after being washed with water, the resultant was condensed to obtain 7.9 g (yield: about 73%) of an oily brown material represented by the following chemical formula.

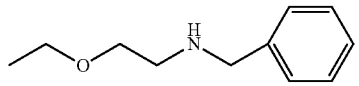

¹H-NMR(CDCl₃):δ1.19 (t,3H),1.77 (br,1H),2.80 (t,2H), 3.48(q,2H),3.55(t,2H), 3.81(s,2H)
IR(NaCl):3027,2974,2866,1495,1453,1376,1114,1028, 735,698cm⁻¹

7.2 g (40 mmol) of the oily orange material was added to 100 ml of dehydrated dichlormethane in a flask followed by Ar gas replacement. Thereafter, 5.9 g (58 mmol) of triethyl amine was added thereto. Next, the system was cooled down to about −10° C. 4.3 g (48 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 3.9 g (yield: about 42%) of an oily, pale yellow material represented by the following chemical formula.

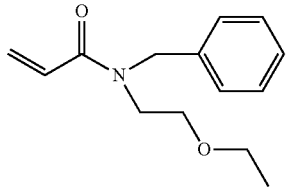

(1-5)

¹H-NMR(CDCl₃):δ1.16(t,3H),3.43(q,2H),3.47(s,2H), 3.63(s,2H), 4.73(d,2H),5.69(dd,1H),6.40(dd,1H),6.50-6.78 (m,1H),7.15-7.36(m,5H)
IR(NaCl):3063,3030,2975,2932,2869,1651,1614,1495, 1443,1356,1262,1221,1117,1060, 1030,979,793,733,699, 518cm⁻¹

Example 9

5.8 g (132 ml) of sodium hydride was added to 140 ml of dehydrated tetrahydrofuran in a flask followed by Ar gas replacement. Thereafter, a solution in which 14.2 g (110 mmol) of 2-(2-hydroxyethyl)piperidine was dissolved in 50 ml of tetrahydrofuran was slowly dropped in the flask at room temperature and the system was stirred for 24 hours at room temperature. Next, after 17.2 g (110 mmol) of ethyl iodide was slowly added while being cooled in water, the system was stirred at room temperature for 24 hours. Furthermore, after filtration, the filtrate was condensed. Next, 100 ml of ethyl acetate was added to the system, the resultant was washed with water. Furthermore, subsequent to drying by sodium sulfate, the dried resultant was condensed under a reduced pressure to obtain 11.7 g (yield: about 67%) of an oily brown material represented by the following chemical formula.

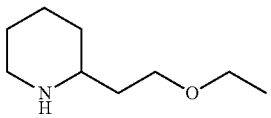

Molecule peak (M+) of MS spectrum (tetrahydrofuran (THF solution): 228 IR (NaCl): 3300,2931,2856,1743,1444, 1375,1239,1115,1048,748,558 cm-1. Since THF (molecular weight: 72) was attached to the molecule ion, the molecule ion peak of the oily brown material (molecular weight: 157) means 156.

10.9 g (69 mmol) of the oily brown material was added to 100 ml of dehydrated dichlormethane in a flask followed by Ar gas replacement. Thereafter, 10.1 g (100 mmol) of triethyl amine was added thereto. Next, the system was cooled down to about −10° C. 7.6 g (84 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 4.9 g (yield: about 33%) of an oily, pale yellow material represented by the following chemical formula.

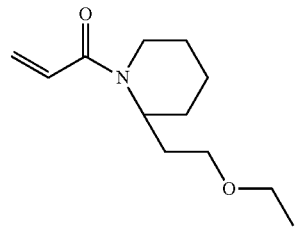

(3-1)

¹H-NMR (CDCl₃):δ1.18(t,3H),1.42(br,1H),1.60-1.80(m, 6H),2.01-2.12(br,1H), 2.62(t,1H),3.20-3.30(m,1H),3.36-3.50(m,4H),4.32(br,1H),4.60(d,1I),5.64(dd,1H),6.26-6.33 (m,1H),6.70-6.80(m,1H)
IR(NaCl):2974,2935,2864,2801,1645,1607,1440,1377, 1356,1333,1262,1212,1177,1137, 1114,1057,1031,997,955, 894,865,836,791,648cm⁻¹

Example 10

9.5 g (83 mmol) of 4-methoxy piperidine was added to 100 ml of dehydrated dichlormethane in a flask followed by Ar gas replacement. Thereafter, 12.0 g (119 mmol) of triethyl amine was added thereto. Next, the system was cooled down to about −10° C. 9.0 g (99 mmol) of acrylic acid chloride was slowly dropped in the system while keeping the temperature in the system ranged from −10° C.

to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 7.2 g (yield: about 53%) of an oily, pale yellow material represented by the following chemical formula.

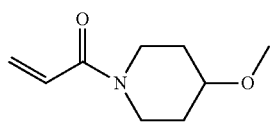

(3-2)

¹H-NMR(CDCl₃):δ1.54-1.62(m,2H),1.83-1.90(m,2H), 3.36(s,3H),3.31-3.49(m,3H), 3.75(br,1H),3.93(br,1H),5.67 (dd,1H),6.25(dd,1H),6.56-6.63(m,1H)
IR(NaCl):2946,2877,2825,1646,1610,1444,1365,1343, 1317,1263,1226,1193,1098,1079, 1023,980,940,884,791, 744,668,558cm⁻¹

Example 11

6.0 g (60 mmol) of 1-methyl piperidine was added to 100 ml of dehydrated dichlormethane in a flask followed by Ar gas replacement. Thereafter, 9.1 g (90 mmol) of triethyl amine was added thereto. Next, the system was cooled down to about −10° C. 6.5 g (72 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material.

Furthermore, by a column chromatography filled with 300 g of Wakogel C300 (manufactured by Wako Pure Chemical Industries, Ltd.) using hexane and ethyl acetate as eluate, the oily brown material was fined to obtain 2.9 g (yield: about 31%) of an oily, pale yellow material represented by the following chemical formula.

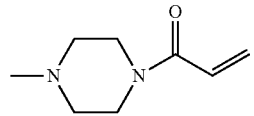

(4-1)

¹H-NMR(CDCl₃):δ2.31(s,3H),3.40 (t,4H),3.60(br,2H), 3.71(br,2H), 5.70(d 1H),6.28(d,1H),6.54-6.20(m,1H)
IR(NaCl):2940,2850,2794,1647,1610,1445,1366,1337, 1293,1254,1230,1172,1144,1074, 1041,1002,980,790,749, 573cm⁻¹

Example 12

9.4 g (65 mmol) of 1-(2-methoxyethyl)piperazine was added to 100 ml of dehydrated dichlormethane in a flask followed by Ar gas replacement. Thereafter, 9.5 g (94 mmol) of triethyl amine was added thereto. Next, the system was cooled down to about −10° C. 7.1 g (78 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 6.8 g (yield: about 53%) of an oily, pale yellow material represented by the following chemical formula.

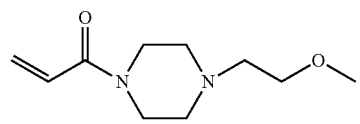

(4-2)

¹H-NMR(CDCl₃):δ2.51(t,4H),2.60(t,2H),3.36(s,3H)3.52 (t,2H), 3.59(br,2H),3.72(br,2H),5.69(d,1H),6.28(d,1H), 6.52-6.60(m,1H)
IR(NaCl):2925,2877,2815,1650,1613,1441,1365,1351, 1307,1236,1151,1115,1071,1041, 1021,1005,963,844, 791cm⁻¹

Example 13

4.1 g (31 mmol) of 1-piperazine ethanol was added to 100 ml of dehydrated dichlormethane in a flask followed by Ar gas replacement. Thereafter, 3.7 g (37 mmol) of triethyl amine was added thereto. Next, the system was cooled down to about −10° C. 2.8 g (31 mmol) of acrylic acid chloride was slowly dropped in the system while keeping the temperature in the system ranged from −10° C. to −5° C. and thereafter stirred for two hours at room temperature. Furthermore, after removal of precipitate by filtration, the filtrate was condensed under a reduced pressure followed by addition of 150 ml of acetone. Next, after removing precipitate by filtration, the filtrate was condensed to obtain 4.3 g of a viscous matter. Furthermore, after 1.6 g (37 mmol) of 55% sodium hydride (containing liquid paraffin) was washed with dehydrated tetrahydrofuran, 40 ml of dehydrated tetrahydrofuran was added and 4.3 g of the viscous matter were thereafter added followed by stirring at room temperature for one hour. Next, 9.4 g (60 mmol) of ethyl iodide was added thereto followed by stirring for 16 hours at room temperature. Thereafter, the system was heated at 66° C. for three hours. Furthermore, after removal of precipitate by filtration, the filtrate was condensed under a reduced pressure to obtain 4.2 g of an oily yellow material.

Furthermore, by a column chromatography filled with 200 g of Wakogel C300 (manufactured by Wako Pure Chemical Industries, Ltd.) using acetone and hexane as eluate, the oily yellow material was fined to obtain 0.8 g (yield: about 12%) of an oily, transparent material represented by the following chemical formula.

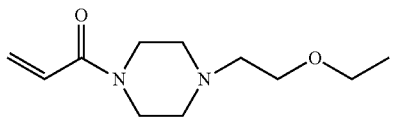

(4-3)

¹H-NMR(CDCl₃):δ1.20(t,3H),2.52(br,4H),2.61(t,2H), 3.51(q,2H)3.57(t,2H), 3.58(br,2H),3.71(br,2H),5.69(d,1H), 6.28(d,1H),6.53-6.59(m,1H)

IR(NaCl):2973,2932,2867,2811,1727,1674,1646,1611, 1442,1387,1351,1304,1238,1112, 1041,1016,1002,980, 792cm⁻¹

Example 14

39.1 g (300 mmol) of 1-piperazine ethanol was added to 250 ml of dehydrated dichlormethane in a flask followed by Ar gas replacement. Thereafter, 36.4 g (360 mmol) of triethyl amine was added thereto. Next, the system was cooled down to about −10° C. 26.3 g (290 mmol) of acrylic acid chloride was slowly dropped in the system while keeping the temperature in the system ranged from −10° C. to −5° C. and thereafter stirred for two hours at room temperature. Furthermore, after removal of precipitate by filtration, the filtrate was condensed under a reduced pressure followed by an addition of 300 ml of acetone and the resultant was preserve in a refrigerator. Furthermore, after removal of precipitate by filtration, the filtrate was condensed under a reduced pressure to obtain 40 g of an oily orange material.

Furthermore, by a column chromatography filled with 300 g of Wakogel C300 (manufactured by Wako Pure Chemical Industries, Ltd.) using acetone and methanol as eluate, the oily orange material was fined to obtain 7.5 g of an oily, pale yellow material represented by the following chemical formula.

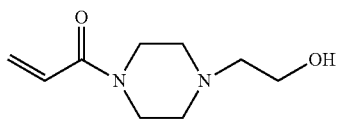

¹H-NMR (CDCl₃):δ2.54(t,4H),2.59(t,2H),2.66(br,1H), 3.59(br,2H), 3.66(t,2H),3.72(br,2H),5.71(d,1H),6.29(d,1H), 6.54-6.59(m,1H)

IR(NaCl):3391,2945,2820,1734,1643,1606,1446,1366, 1305,1249,1148,1052,1012,1000, 979,910,875,792,767, 751cm⁻¹

4.6 g (25 mmol) of the oily, pale yellow material was added to 70 ml of dehydrated dichlormethane in a flask followed by Ar gas replacement. Thereafter, 4.1 g (40 mmol) of triethyl amine was added thereto. Next, the system was cooled down to about −10° C. 2.8 g (30 mmol) of propionic acid chloride was slowly dropped in the system while keeping the temperature in the system ranged from −10° C. to −5° C. and thereafter stirred for two hours at room temperature. Furthermore, after removal of precipitate by filtration, the filtrate was condensed under a reduced pressure followed by an addition of 100 ml of ethyl acetate for extraction. The resultant was condensed under a reduced pressure to obtain 6.1 g of oily yellow material. Furthermore, by a column chromatography filled with 200 g of Wakogel C300 (manufactured by Wako Pure Chemical Industries, Ltd.) using acetone and ethyl acetate as eluate, the oily brown material was fined to obtain 3.1 g (yield: about 52%) of an oily, pale yellow material represented by the following chemical formula.

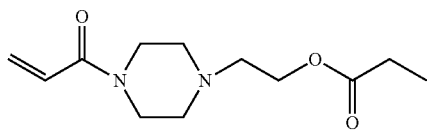

(4-4)

¹H-NMR(CDCl₃):δ1.14(t,3H),2.34(q,2H),2.52(t,4H), 2.66(t,2H), 3.57(br,2H),3.70(br,2H),4.22(t,2H),5.69(d,1H), 6.28(d,1H),6.53-6.59(m, 1H)

IR(NaCl):2943,2817,1736,1647,1611,1444,1368,1347, 1307,1235,1187,1085,1017,1004, 972,791cm⁻¹

Example 15

6.3 g (40 mmol) of 1-piperazine ethylcarbonate was added to 100 ml of dehydrated dichlormethane in a flask followed by Ar gas replacement. Thereafter, 6.1 g (60 mmol) of triethyl amine was added thereto. Next, the system was cooled down to about −10° C. 4.3 g (48 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material.

Furthermore, by a column chromatography filled with 300 g of Wakogel C300 (manufactured by Wako Pure Chemical Industries, Ltd.) using hexane and ethyl acetate as eluate, the oily brown material was fined to obtain 4.1 g (yield: about 48%) of an oily, pale yellow material represented by the following chemical formula.

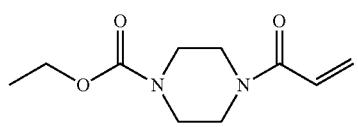

(4-5)

¹H-NMR(CDCl₃):δ1.28(t,3H),3.47-3.53(m,4H),3.55(br, 2H),3.67(br,2H), 4.16(q,4H),5.73(dd,1H),6.31(dd,1H),6.53-6.61(m,1H)

IR(NaCl):2983,2909,2865,1703,1651,1614,1434,1385, 1354,1281,1232,1173,1126,1082, 1033,990,924,872,825, 791,768,543cm⁻¹

Example 16

12.6 g (80 mmol) of ethyl nipecotiate was added to 100 ml of dehydrated dichloromethane in a flask followed by Ar gas replacement. Thereafter, 11.6 g (115 mmol) of triethyl amine was added thereto. Next, the system was cooled down to about −10° C. 8.7 g (96 mmol) of acrylic acid chloride was slowly dropped in the system while keeping the temperature in the system ranged from −10° C. to −5° C. and thereafter stirred for two hours at room temperature.

Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material.

Furthermore, by a column chromatography filled with 300 g of Wakogel C300 (manufactured by Wako Pure Chemical Industries, Ltd.) using hexane and ethyl acetate as eluate, the oily brown material was fined to obtain 9.1 g (yield: about 53%) of an oily, pale yellow material represented by the following chemical formula.

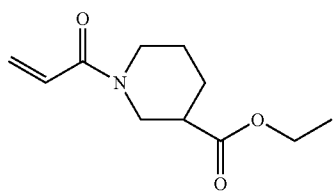

(3-3)

$^1$H-NMR(CDCl$_3$):δ1.26(s,2H),1.43-1.59(m,1H),1.63-1.88(m,2H),2.00-2.20(m 2H),2.44-2.54(m,1H),3.06-3.24(m,1H),3.48-3.58(m,1H),3.82-3.94 (d,1H),4.14(q,2H), 5.69 (d,1H),6.27(d,1H),6.53-6.71(m,1H)

IR(NaCl):2981,2941,2863,1731,1650,1614,1442,1378, 1301,1255,1226,1179,1120,1030, 1009,978,857,791, 623cm$^{-1}$

Example 17

7.9 g (50 mmol) of 4-piperidine ethylcarbonate was added to 100 ml of dehydrated dichlormethane in a flask followed by Ar gas replacement. Thereafter, 7.3 g (72 mmol) of triethyl amine was added thereto. Next, the system was cooled down to about −10° C. 5.4 g (60 mmol) of acrylic acid chloride was slowly dropped in the system while keeping the temperature in the system ranged from −10° C. to −5° C. and thereafter stirred for two hours at room temperature.

Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 5.4 g (yield: about 51%) of an oily, pale yellow material represented by the following chemical formula.

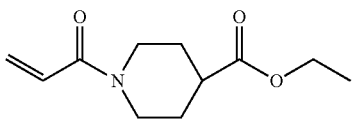

(3-4)

$^1$H-NMR(CDCl$_3$):δ1.26(t,3H),1.70(m,2H),1.94(m,2H), 2.56(m,1H), 2.91(t,1H),3.16(t,1H),3.90(d,1H),4.14(m,2H), 4.44(d,1H),5.67(dd,1H),6.25(dd,1H),6.54-6.61(m,1H)

IR(NaCl):3475,2981,2956,2862,1729,1646,1611,1448, 1377,1316,1264,1179,1097,1042, 980,950,921,863,792, 619,526cm$^{-1}$

Comparative Example 1

Acryloyl morpholine represented by the following chemical formula, available on the market, was used.

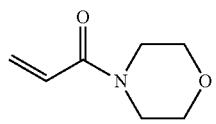

Comparative Example 2

N—N-diethylacrylamide represented by the following chemical formula, available on the market, was used.

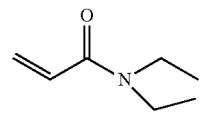

Comparative Example 3

N-(3-dimethylaminopropyl)acrylamide represented by the following chemical formula, available on the market, was used.

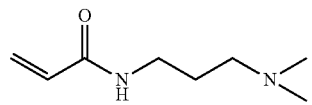

Comparative Example 4

N-(2-hydroxyethyl)acrylamide represented by the following chemical formula, available on the market, was used.

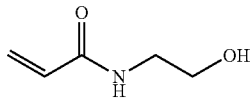

Comparative Example 5

N—N'-methylene bisacrylamide represented by the following chemical formula, available on the market, was used.

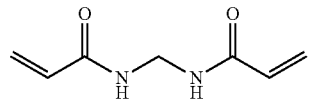

Comparative Example 6

9.1 g (50 mmol) of dicyclohexyl amine was added to 100 ml of dehydrated dichloromethane in a flask followed by Ar gas replacement. Thereafter, 7.3 g (72 mmol) of triethyl amine was added thereto. Next, the system was cooled down to about −10° C. 5.4 g (60 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 8.0 g (yield: about 68%) of a pale yellow crystal represented by the following chemical formula.

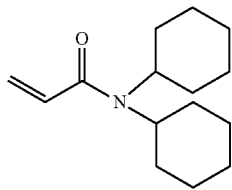 [SMILES: C=CC(=O)N(C1CCCCC1)C1CCCCC1]

$^1$H-NMR(CDCl$_3$):δ1.01-1.04 (m,8H),1.05-1.08(m,12H), 2.89(br,1H),3.51(br,1H), 5.56(d,1H),6.18(d,1H),6.80-6.90 (m,1H)

IR(NaCl):3095,2930,2854,1646,1607,1469,1439,1396, 1350,1303,1264,1237,1224,1184, 1145,1126,1055,1028, 995,979,952,895,844,820,791,756,677,614cm$^{-1}$

Comparative Example 7

5.3 g (40 mmol) of 1,2,3,4-tetrahydroisoquinoline was added to 100 ml of dehydrated dichloromethane in a flask followed by Ar gas replacement. Thereafter, 6.1 g (60 mmol) of triethyl amine was added thereto. Next, the system was cooled down to about −10° C. 4.3 g (48 mmol) of acrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material.

Furthermore, by a column chromatography filled with 300 g of Wakogel C300 (manufactured by Wako Pure Chemical Industries, Ltd.) using hexane and ethyl acetate as eluate, the oily brown material was fined to obtain 3.9 g (yield: about 54%) of an oily yellow material represented by the following chemical formula.

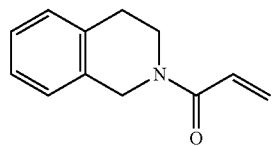

1H-NMR(CDCl3):δ2.84-2.94(m,2H),3.82(dt,2H),4.76(d, 2H),5.72(d,1H),6.33(d,1H), 6.60-6.70(m, 1H),7.06-7.24(m, 4H)

IR(NaCl):3023,2928,2898,2842,1650,1613,1583,1496, 1444,1384,1365,1346,1294,1278, 1245,1211,1111,1055, 1038,977,933,828,792,763,745,660,600,568cm$^{-1}$

Comparative Example 8

5.3 g (40 mmol) of 1,2,3,4-tetrahydroisoquinoline was added to 100 ml of dehydrated dichloromethane in a flask followed by Ar gas replacement. Thereafter, 6.1 g (60 mmol) of triethyl amine was added thereto. Next, the system was cooled down to about −10° C. 5.0 g (48 mmol) of methacrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 5.2 g (yield: about 68%) of an oily yellow material represented by the following chemical formula.

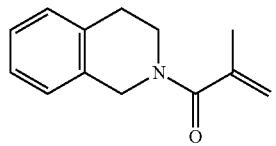

$^1$H-NMR(CDCl$_3$):δ1.99(s,3H),2.88(s,2H),3.80(d,2H), 4.74(d,21-1),5.09 (s,1H), 5.23(s,1H),7.00-7.25(m,4H)

IR(NaCl):3081,3022,2976,2921,2843,1647,1622,1584, 1497,1435,1371,1343,1302,1277, 1247,1182,1110,1055, 1039,1015,981,929,826,754,628,557cm$^{-1}$

Comparative Example 9

6.0 g (60 mmol) of 1-methyl piperidine was added to 100 ml of dehydrated dichloromethane in a flask followed by Ar gas replacement. Thereafter, 9.1 g (90 mmol) of triethyl amine was added thereto. Next, the system was cooled down to about −10° C. 7.5 g (72 mmol) of methacrylic acid chloride was slowly dropped in the system while keeping the temperature in the system ranged from −10° C. to −5° C. and thereafter stirred for two hours at room temperature.

Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material. Furthermore, by a column chromatography filled with 300 g of Wakogel C300 (manufactured by Wako Pure Chemical Industries, Ltd.) using hexane and ethyl acetate as eluate, the oily brown material was fined to obtain 5.7 g (yield: about 56%) of an oily yellow material represented by the following chemical formula.

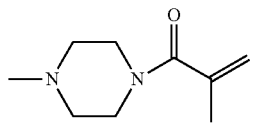

$^1$H-NMR(CDCl$_3$):δ1.96(s,3H),2.32(s,3H),2.41(br,4H), 3.50-3.80(br,4H),5.03(br,1H), 5.19(br,1H)

IR(NaCl):3081,2972,2939,2847,2791,2742,1650,1626, 1462,1434,1370,1303,1290,1246, 1203,1172,1142,1072, 1038,1002,912,779,616,561cm$^{-1}$

Comparative Example 10

6.3 g (40 mmol) of 1-piperazine ethylcarbonate was added to 100 ml of dehydrated dichloromethane in a flask followed by Ar gas replacement. Thereafter, 6.1 g (60 mmol) of triethyl amine was added thereto. Next, the system was cooled down to about −10° C. 5.0 g (48 mmol) of methacrylic acid chloride was slowly dropped in the system while keeping the temperature in the system ranged from −10° C. to −5° C. and thereafter stirred for two hours at room temperature. Furthermore, subsequent to removal of precipitants by filtration, the filtrate was washed with saturated sodium hydrogen carbonate aqueous solution and saturated sodium chloride aqueous solution. Next, subsequent to drying by sodium sulfate, the dried resultant was condensed under a reduced pressure to obtain an oily brown material.

Furthermore, by a column chromatography filled with 300 g of Wakogel C300 (manufactured by Wako Pure Chemical Industries, Ltd.) using hexane and ethyl acetate as eluate, the oily brown material was fined to obtain 7.3 g (yield: about 81%) of an oily, pale yellow material represented by the following chemical formula.

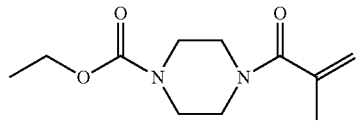 [SMILES: C=C(C)C(=O)N1CCN(C(=O)OCC)CC1]

$^1$H-NMR(CDCl$_3$):δ1.29(t,3H),1.96 (t,3H),3.48(br,4H), 3.57(br,4H),4.17(q,2H), 5.04(d,1H),5.22(d,1H)

IR(NaCl):3082,2982,2916,2864,1698,1650,1622,1470, 1430,1386,1355,1283,1253,1233, 1198,1174,1125,1080, 1030,1006,990,918,870,826,769,596,562,541cm$^{-1}$

Manufacturing of Photopolymerizable Composition 950 mg of the photopolymerizable compounds of Examples and Comparative Examples and 50 mg of a photopolymerization initiator (IRGACURE 907: 2-methyl-1-[4-(methylthio)phenyl]-2-morpholinopropane-1-one, manufactured by BASF Japan Ltd.) were mixed by a magnetic stirrer to prepare photopolymerizable compositions.

Next, the viscosity and the odor of the photopolymerizable compounds were evaluated.

In addition, using the photopolymerizable compound, the photopolymerizability and photocurability of the photopolymerizable compound were evaluated.

Viscosity

Using a viscoelasticity measuring instrument VAR200AD, manufactured by REOLOGICA, the viscosity of the photopolymerizable compound at 25° C. was measured. A plate of having a diameter of 40 mm was used for the measuring.

Odor

The odor of the photopolymerizable compound was evaluated according to the following procedure. The criteria of evaluating the odor of the photopolymerizable compound are as follows:

A: Order sensed but not uncomfortable
B: Uncomfortable peculiar odor
C: Particularly uncomfortable peculiar odor
(1): About 100 g (0.1 g) of a photopolymerizable compound was weighed and put in a 50 cc glass bottle and the lid thereof was closed.
(2): The glass bottle was left at room temperature for about 30 minutes.
(3): Thereafter, the lid was opened to smell the odor by nose.

Photopolymerizability

The photopolymerizability of the photopolymerizable compound was measured by using a measuring instrument formed by a combination of DSC-7020 (manufactured by Seiko Instruments Inc.) and a spot light source LA-410 UV (manufactured by Hayashi Watch-Works Co., Ltd.) for evaluation. Specifically, the amount of generated heat was measured for one sample when the photopolymerizable compound in the photopolymerizable composition was exposed to ultraviolet ray having a wavelength of 365 nm with 200 mW/cm$^2$ for a sufficient time to complete polymerization. The generated heat obtained in the measuring included the generated heat accompanied by ultraviolet irradiation in addition to the heat generated accompanied by the polymerization of the photopolymerizable compound. Therefore, to the sample which had been polymerized for measuring, the sample was exposed to ultraviolet ray again under the same condition to measure the amount of generated heat other than the amount of generated heat accompanied by the polymerization of the photopolymerizable compound. The amount of generated heat accompanied by the polymerization of the photopolymerizable compound from the difference between the amounts of generated heat for the first time and the second time. T$_1$(s), which was defined as the time from the start of irradiation of ultraviolet ray to when the amount of generated heat reached the maximum, was used as an index to compare the speed of photopolymerization.

Photocurability

The photocurability of the photopolymerizable compound was evaluated by using a measuring instrument formed by a combination of a viscoelasticity measuring instrument (VAR 200 AD, manufactured by REOLOGICA) and an LED light source (LIGHTNINGCURE LC-L1, manufactured by Hamamatsu Photonics K.K.). Specifically, after nipping a photopolymerizable composition with a gap of 10 μm using a cone plate having a diameter of 20 mm, the photopolymerizable composition was exposed to ultraviolet ray having a wavelength of 365 nm with 50 mW/cm$^2$ to measure the change of the elasticity thereof until the elasticity was saturated. Based on the measuring results, the maximum value of the elasticity was obtained, which was defined as index of curing level. Normally, when a material has a coefficient of elasticity of 1×10$^4$ Pa, the curing level thereof is said to be sufficient. In addition, the energy of ultraviolet ray to which the compound is exposed until the coefficient of elasticity is saturated, i.e., curing energy, is calculated by multiplying an intensity (50 mW/cm$^2$) of ultraviolet ray with irradiation time (s) of ultraviolet ray.

The evaluation results of the viscosity, the odor, the photopolymerizability, and the photocurability of the photopolymerizable compounds are shown in Table 1.

TABLE 1

|  | Viscosity (mPa·s) | Odor | Photopolymerizability T1 (s) | Photo-curability | |
|---|---|---|---|---|---|
|  |  |  |  | Elasticity (×10$^5$ Pa) | Curing energy (mJ/cm$^2$) |
| Example 1 | 2 | A | 5.4 | 1.0 | 321 |
| Example 2 | 3 | A | 4.8 | 0.9 | 428 |
| Example 3 | 4 | A | 3.6 | 0.8 | 382 |
| Example 4 | 4 | A | 5.4 | 1.0 | 309 |
| Example 5 | 46 | A | 5.4 | 1.0 | 232 |
| Example 6 | 27 | A | 3.6 | 1.0 | 119 |
| Example 7 | 12 | A | 3.6 | 1.0 | 128 |
| Example 8 | 21 | A | 5.0 | 1.0 | 300 |
| Example 9 | 11 | A | 3.6 | 1.0 | 147 |
| Example 10 | 9 | A | 4.9 | 1.0 | 265 |
| Example 11 | 6 | A | 5.1 | 1.0 | 280 |
| Example 12 | 13 | A | 4.8 | 1.0 | 158 |
| Example 13 | 9 | A | 3.6 | 0.7 | 250 |
| Example 14 | 86 | A | 3.0 | 1.0 | 130 |
| Example 15 | 81 | A | 4.2 | 1.0 | 130 |
| Example 16 | 13 | A | 3.0 | 1.0 | 110 |
| Example 17 | 12 | A | 2.8 | 1.0 | 101 |
| Comparative Example 1 | 6 | B | 6.5 | 1.0 | 190 |
| Comparative Example 2 | 2 | C | 4.8 | 1.0 | 208 |
| Comparative Example 3 | 70 | C | 3.6 | 1.0 | 244 |
| Comparative Example 4 | 128 | A | — | — | — |
| Comparative Example 5 | — | B | — | — | — |
| Comparative Example 6 | — | A | — | — | — |
| Comparative Example 7 | 436 | A | 7.0 | 1.0 | 2,744 |
| Comparative Example 8 | 505 | A | — | — | — |
| Comparative Example 9 | 6 | A | — | — | — |
| Comparative Example 10 | 410 | A | — | — | — |

As seen in Table 1, the photopolymerizable compounds of Examples 1 to 17 had excellent photopolymerizability and photocurability with less odor and viscosity.

However, the photopolymerizable compound of Comparative Example 1 had odor since it had a morpholino group.

The photopolymerizable compound of Comparative Example 2 had odor significantly because it had no carbonyl imino group or polar group in the ethyl group bonded with a nitrogen atom.

The photopolymerizable compound of Comparative Example 3 had odor significantly because it had a carbonyl imino group and a dimethyl amino group.

Since the photopolymerizable compound of Comparative Example 4 had a carbonyl imino group and a hydroxyl group so that the viscosity thereof was high, the photopolymerization initiator was not dissolved in the photopolymerizable compound, thereby failing to obtain a photopolymerizable composition.

Since the photopolymerizable compound of Comparative Example 5 had two carbonyl imino groups, it was solid at room temperature, so that a photopolymerizable composition was not manufactured.

Since the photopolymerizable compound of Comparative Example 6 had no carbonyl imino group and the two cyclohexane groups were bonded by a nitrogen atom, it was solid at room temperature, so that a photopolymerizable composition was not manufactured.

Since the photopolymerizable compounds of Comparative Examples 7 and 8 had no carbonyl imino group and a monovalent group containing a polar group was not bonded to a ring containing a nitrogen atom, the photopolymerizable compound had a high viscosity and low curability.

The photopolymerizable compounds of Comparative Examples 8 to 10 were methacrylic amides, it was not photopolymerized, so that no photocuring occurred.

Since the nitrogen atom in the photopolymerizable compound of Comparative Example 10 was replaced with an ethyloxycarbonyl group, it had a high viscosity.

Preparation of Ink 100 parts of the photopolymerizable compounds of Examples 1 to 17, 10 parts of a photopolymerization initiator (IRGACURE 907, manufactured by BASF Japan), and 3 parts of carbon black MICROLITH Black C-K (manufactured by BASF Japan) were mixed to obtain Ink 1.

100 parts of the photopolymerizable compounds of Examples 1 to 17, 10 parts of a photopolymerization initiator (IRGACURE 907, manufactured by BASF Japan), and 3 parts of carbon black MICROLITH Blue 4G-K (manufactured by BASF Japan) were mixed to obtain Ink 2.

Evaluation of Ink 1

After discharging ink on a slide glass, the ink was exposed to ultraviolet ray having a wavelength of 365 nm with 200 mW/cm$^2$ using a UV irradiator LH6 (manufactured by Heraeus Noblelight Fusion UV) for curing.

As a consequence, it was confirmed Ink 1 and 2 were dischargeable and the ink images were sufficiently cured.

Evaluation of Ink 2

The tip of a dip pen was dipped in ink and texts were written on a PET film and plain paper. Thereafter, the texts were exposed to ultraviolet ray having a wavelength of 365 nm with 200 mW/cm$^2$ using a UV irradiator LH6 (manufactured by Heraeus Noblelight Fusion UV) for curing. As a consequence, it was confirmed the ink images of Ink 1 and 2 were sufficiently cured.

According to the present disclosure, a compound, ink and a composition that contain the ink, which have excellent polymerization property and photo-curability with less odor and small viscosity are provided.

Having now fully described embodiments of the present invention, it will be apparent to one of ordinary skill in the art that many changes and modifications can be made thereto without departing from the spirit and scope of embodiments of the invention as set forth herein.

What is claimed is:

1. Ink comprising:
   at least one of a compound represented by chemical formula 1, a compound represented by chemical formula 2, a compound represented by chemical formula 3, or a compound represented by chemical formula 4, Chemical formula 1

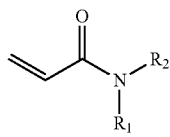
(1)

where $R_1$ represents a hydrocarbon group having 1 to 10 carbon atoms and $R_2$ represents a monovalent group comprising one functional group selected from the group consisting of a group represented by —$COOX_2$, where $X_2$ represents a monovalent hydrocarbon group having 1 to 10 carbon atoms, a group represented by —$OCOX_3$, where $X_3$ represents a monovalent hydrocarbon group having 1 to 10 carbon atoms, and a group represented by —$NX_4X_5$, where $X_4$ and $X_5$ each, independently represent monovalent hydrocarbon groups having 1 to 10 carbon atoms, Chemical formula 2

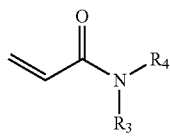
(2)

where, $R_3$ and $R_4$ each, independently represent monovalent groups comprising groups represented by —$OX_1$, where $X_1$ represents a monovalent hydrocarbon group having 1 to 10 carbon atoms, a monovalent group comprising a group represented by —$COOX_2$, where $X_2$ represents a monovalent hydrocarbon group having 1 to 10 carbon atoms, a monovalent group comprising a group represented by —$OCOX_3$, where $X_3$ represents a monovalent hydrocarbon group having 1 to 10 carbon atoms, a monovalent group comprising a group represented by —$NX_4X_5$, where $X_4$ and $X_5$ each, independently represent monovalent hydrocarbon groups having 1 to 10 carbon atoms, a monovalent group comprising a group represented by —$CONX_6X_7$, where $X_6$ and $X_7$ each, independently represent monovalent hydrocarbon groups having 1 to 10 carbon atoms, or a monovalent group comprising a hydroxyl group, Chemical formula 3

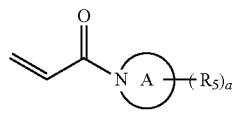
(3)

where a ring A represents a saturated five-membered ring or a saturated six-membered ring, both comprising a nitrogen atom, $R_5$ represents a monovalent group comprising a group represented by —$OX_1$, where $X_1$ represents a monovalent hydrocarbon group having 1 to 10 carbon atoms, a monovalent group comprising a group represented by —$COOX_2$, where $X_2$ represents a monovalent hydrocarbon group having 1 to 3 carbon atoms other than a t-butyl group, a monovalent group comprising a group represented by —$OCOX_3$, where $X_3$ represents a monovalent hydrocarbon group having 1 to 10 carbon atoms, a monovalent group comprising a group represented by —$NX_4X_5$, where $X_4$ and $X_5$ each, independently represent monovalent hydrocarbon groups having 1 to 10 carbon atoms, a monovalent group comprising a group represented by —$CONX_6X_7$, where $X_6$ and $X_7$ each, independently represent monovalent hydrocarbon groups having 1 to 10 carbon atoms, or a monovalent group comprising a hydroxyl group, and a is 1, 2, or 3, and Chemical formula 4

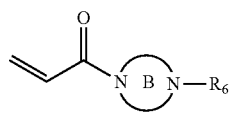
(4)

where a ring B represents a saturated five-membered ring or a saturated six-membered ring, both comprising two nitrogen atoms, $R_6$ represents a monovalent group comprising a group represented by —$OX_1$, where $X_1$ represents a monovalent hydrocarbon group having 1 to 10 carbon atoms, a monovalent group comprising a group represented by —$COOX_2$, where $X_2$ represents a monovalent hydrocarbon group having 1 to 10 carbon atoms, a monovalent group comprising a group represented by —$OCOX_3$, where $X_3$ represents a monovalent hydrocarbon group having 1 to 10 carbon atoms, a monovalent group comprising a group represented by —$NX_4X_5$, where $X_4$ and $X_5$ each, independently represent monovalent hydrocarbon groups having 1 to 10 carbon atoms, a monovalent group comprising a group represented by —$CONX_6X_7$, where $X_6$ and $X_7$ each, independently represent monovalent hydrocarbon groups having 1 to 10 carbon atoms, a monovalent group comprising a hydroxyl group, or an alkyl group having 1 to 10 carbon atoms, wherein, in each of Chemical Formula 2, 3, and 4, when $R_3$, $R_4$, and $R_6$ represents —$OX_1$, —$OX_1$ is bound to the nitrogen atom through an alkylene group that has at least three carbon atoms, and a viscosity of the ink ranges from 7 mPa·s to 30 mPa·s.

2. The ink according to claim 1, wherein the ink comprises the compound represented by chemical formula 1, wherein $R_1$ represents a cycloalkyl group, an aryl group, or an aralkyl group.

3. The ink according to claim 1, wherein $R_3$ and $R_4$ each independently represent 2-hydroxyethyl group.

4. The ink according to claim 1, wherein the ink comprises the compound represented by chemical formula 3, which is represented by chemical formula 6

Chemical formula 6

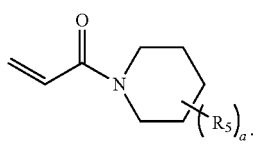
(6)

5. The ink according to claim 4, wherein $R_5$ is a group represented by —$COOX_2$, where $X_2$ represents a hydrocarbon group having 1 to 10 carbon atoms other than a t-butyl group.

6. An ink cartridge comprising:
the ink of claim 1; and
a container to accommodate the ink.

7. An ink jet recording device comprising:
a discharging device comprising the ink of claim 1 to discharge the ink.

8. An ink jet ink printed matter comprising:
an image of the ink of claim 1; and
a recording medium on which the image is formed.

9. The ink according to claim 1, which further comprises at least one of:
a photopolymerization initiator; and
a colorant.

10. The ink according to claim 1, which further comprises:
a photopolymerization initiator; and
a colorant.

11. The ink according to claim 1, wherein the ink comprises the compound represented by chemical formula 4, wherein,
in formula 4, the nitrogen atom of ring B bound to $R_6$ is bound to $R_6$ through a —$(CH_2)_m$— linker group, where m represents an integer of from 1 to 6.

12. The ink according to claim 1, wherein the ink comprises the compound represented by chemical formula 3, wherein in formula 3, a is 2 or 3.

13. The ink according to claim 1, wherein the ink does not comprise a solvent.

14. The ink according to claim 1, wherein the ink comprises an organic solvent in an amount of from 0.1% by weight to 5% by weight.

* * * * *